United States Patent
Yamanaka et al.

(10) Patent No.: US 10,543,049 B2
(45) Date of Patent: Jan. 28, 2020

(54) MEDICAL MANIPULATOR

(71) Applicant: OLYMPUS CORPORATION, Tokyo (JP)

(72) Inventors: Noriaki Yamanaka, Tokyo (JP); Toshihiro Yoshii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 540 days.

(21) Appl. No.: 14/828,945

(22) Filed: Aug. 18, 2015

(65) Prior Publication Data

US 2016/0038239 A1    Feb. 11, 2016

Related U.S. Application Data

(63) Continuation of application No. PCT/JP2014/053233, filed on Feb. 5, 2014.

(60) Provisional application No. 61/766,810, filed on Feb. 20, 2013.

(51) Int. Cl.
  *A61B 34/37*    (2016.01)
  *A61B 17/29*    (2006.01)
  *A61B 17/00*    (2006.01)

(52) U.S. Cl.
  CPC .... *A61B 34/37* (2016.02); *A61B 2017/00199* (2013.01); *A61B 2017/2932* (2013.01); *A61B 2017/2943* (2013.01)

(58) Field of Classification Search
  CPC ......... A61B 34/30; A61B 34/70; A61B 34/71; A61B 34/72; A61B 2034/301; A61B 2034/302; A61B 2034/303; A61B 2034/32; A61B 2034/35; A61B 2034/37; A61B 17/2909; A61B 2017/2912;
  (Continued)

(56) References Cited

U.S. PATENT DOCUMENTS 5,964,717 A * 10/1999 Gottlieb ................. A61B 10/06
                                                           600/567
6,497,651 B1  12/2002 Kan et al.
(Continued)

FOREIGN PATENT DOCUMENTS

EP    1 886 630 A2    2/2008
EP    2 329 773 A1    6/2011
(Continued)

OTHER PUBLICATIONS

Extended Supplementary European Search Report dated Aug. 22, 2016 in related European Application No. 14 75 3689.0.
(Continued)

*Primary Examiner* — Diane D Yabut
(74) *Attorney, Agent, or Firm* — Scully, Scott, Murphy & Presser, P.C.

(57) ABSTRACT

In a medical manipulator, the surgical tool drive unit includes: a pair of input members that has a first input member and a second input member, are arranged in a pair at a first end portion in an attachment and detachment direction with respect to the surgical tool unit, are capable of advancing and retracting parallel to each other, and transmit the driving force in an advance direction when the pair of input members are advanced to the surgical tool unit side; and a drive source that causes at least one of the pair of input members to advance and retract.

10 Claims, 22 Drawing Sheets

(58) Field of Classification Search
CPC .... A61B 2017/2923; A61B 2017/2932; A61B 2017/2937
See application file for complete search history.

(56) References Cited

U.S. PATENT DOCUMENTS

| | | | |
|---|---|---|---|
| 8,333,780 B1* | 12/2012 | Pedros | A61B 17/29 600/37 |
| 2012/0083826 A1 | 4/2012 | Chao et al. | |
| 2013/0012959 A1* | 1/2013 | Jinno | A61B 17/29 606/130 |

FOREIGN PATENT DOCUMENTS

| | | |
|---|---|---|
| JP | 3686947 B2 | 8/2005 |
| JP | 2007-029274 A | 2/2007 |
| JP | 5800676 B2 | 9/2015 |
| KR | 10-2012-0108416 A | 10/2012 |
| WO | 2006/137255 A1 | 12/2006 |
| WO | 2013-018926 A1 | 2/2013 |
| WO | WO 2013/062132 A1 | 5/2013 |

OTHER PUBLICATIONS

International Search Report dated May 13, 2014 issued in PCT/JP2014/053233.
Japanese Office Action dated Jun. 7, 2016 in related Japanese Patent Application No. 2015-541352.

\* cited by examiner

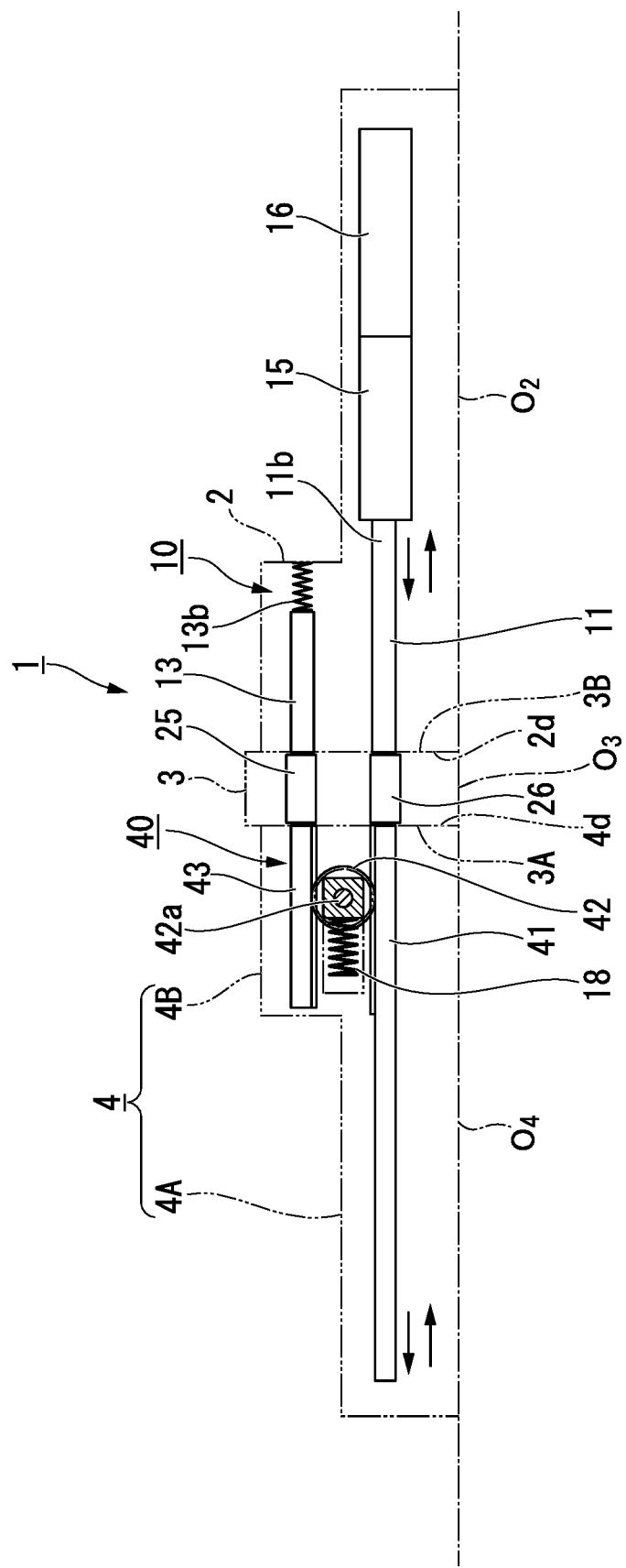

MEDICAL MANIPULATOR

This application is a communication application based on PCT application No. PCT/JP2014/053233 filed on Feb. 5, 2014, whose priority is claimed on U.S. Patent Application No. 61/766,810, provisionally applied in the United States on Feb. 20, 2013. The contents of both the PCT application and U.S. Provisional Application are incorporated herein by reference.

TECHNICAL FIELD

The present invention relates to a medical manipulator.

BACKGROUND ART

In the related art, medical manipulators for performing surgery assistance for a surgical operation are known.

In such medical manipulators, in order to sterilize surgical tool units, it is necessary to detachably provide the surgical tool units and surgical tool drive units.

For example, Patent Document 1 describes active forceps provided in which a forceps distal end part structure and a forceps shaft portion, which are a surgical tool unit, are detachably provided with respect to a forceps proximal end part, which is a surgical tool drive unit, at a proximal end portion of the forceps shaft portion, as such a medical manipulator.

In the active forceps described in Japanese Patent No. 3686947, for mounting of the surgical tool unit, the forceps shaft portion is fixed to a frame by tightening a fastening screw of a clamp after the forceps shaft portion is inserted into the frame of the forceps proximal end part and is rotated at 60 degrees around the central axis of the frame to hook a hooking member to a holder.

SUMMARY OF THE INVENTION

A medical manipulator according to a first aspect of the present invention includes: a surgical tool unit that is provided with an effector that operates an operation target; and a surgical tool drive unit that is detachably provided with respect to the surgical tool unit and supplies a driving force for driving the effector. The surgical tool drive unit includes: a pair of input members that has a first input member and a second input member, are arranged in a pair at a first end portion in an attachment and detachment direction with respect to the surgical tool unit, are capable of advancing and retracting parallel to each other, and transmit the driving force in an advance direction when the pair of input members are advanced to the surgical tool unit side; and a drive source that causes at least one of the pair of input members to advance and retract. The surgical tool unit includes: a first transmission member that faces the first input member, is supported so as to be capable of advancing and retracting at a first end portion in the attachment and detachment direction with respect to the surgical tool drive unit, moves in a same direction as an advance direction of the first input member under the driving force from the first input member, and is connected to the effector at a second end portion; a second transmission member that faces the second input member, is supported so as to be capable of advancing and retracting at the first end portion in the attachment and detachment direction with respect to the surgical tool drive unit, and moves in a same direction as an advance direction of the second input member under the driving force from the second input member; and a surgical-tool-unit-side reversal interlinking member that is engaged with the first transmission member and the second transmission member, and reverses a moving direction of the first transmission member or the second transmission member and transmits a displacement of one of the first transmission member and the second transmission member to the other of the first transmission member and the second transmission member.

According to a second aspect of the present invention, in the medical manipulator of the first aspect, the first input members may be capable of advancing and retracting by being connected to the drive source. The surgical tool unit may further include a drive-unit-side reversal interlinking member that is engaged with the first input member and the second input member, and reverses a moving direction of the first transmission member or the second transmission member and transmits a displacement of the first input member to the second input member, wherein the drive-unit-side reversal interlinking member is provided between the first input member and the second input member.

According to a third aspect of the present invention, in the medical manipulator of the second aspect, an engaging and disengaging mechanism may be further included that moves the drive-unit-side reversal interlinking member with respect to the pair of input members so as to switch a state of being engaged with the first input member and the second input member and a state where a transmission of a displacement between the first input member and the second input member is released.

According to a fourth aspect of the present invention, in the medical manipulator any one of the first aspect to the third aspect, the surgical tool drive unit may have a drive-unit-side biasing member that biases the pair of input members toward the first end portion in the attachment and detachment direction with respect to the surgical tool unit.

According to a fifth aspect of the present invention, in the medical manipulator of the fourth aspect, the drive-unit-side biasing member may have a first drive-unit-side biasing member and a second drive-unit-side biasing member, and the first drive-unit-side biasing member may be provided in the first input member and the second drive-unit-side biasing member is provided in the second input member.

According to a sixth aspect of the present invention, in the medical manipulator any one of the first aspect to the fifth aspect, a second biasing member may be further included that biases both of the first input member and the second input member, toward the first end portion in the attachment and detachment direction with respect to the surgical tool unit.

BRIEF DESCRIPTION OF DRAWINGS

FIG. 15 is a schematic configuration view of main portions of the medical manipulator of the first embodiment of the present invention.

DESCRIPTION OF EMBODIMENTS

Figure 1:
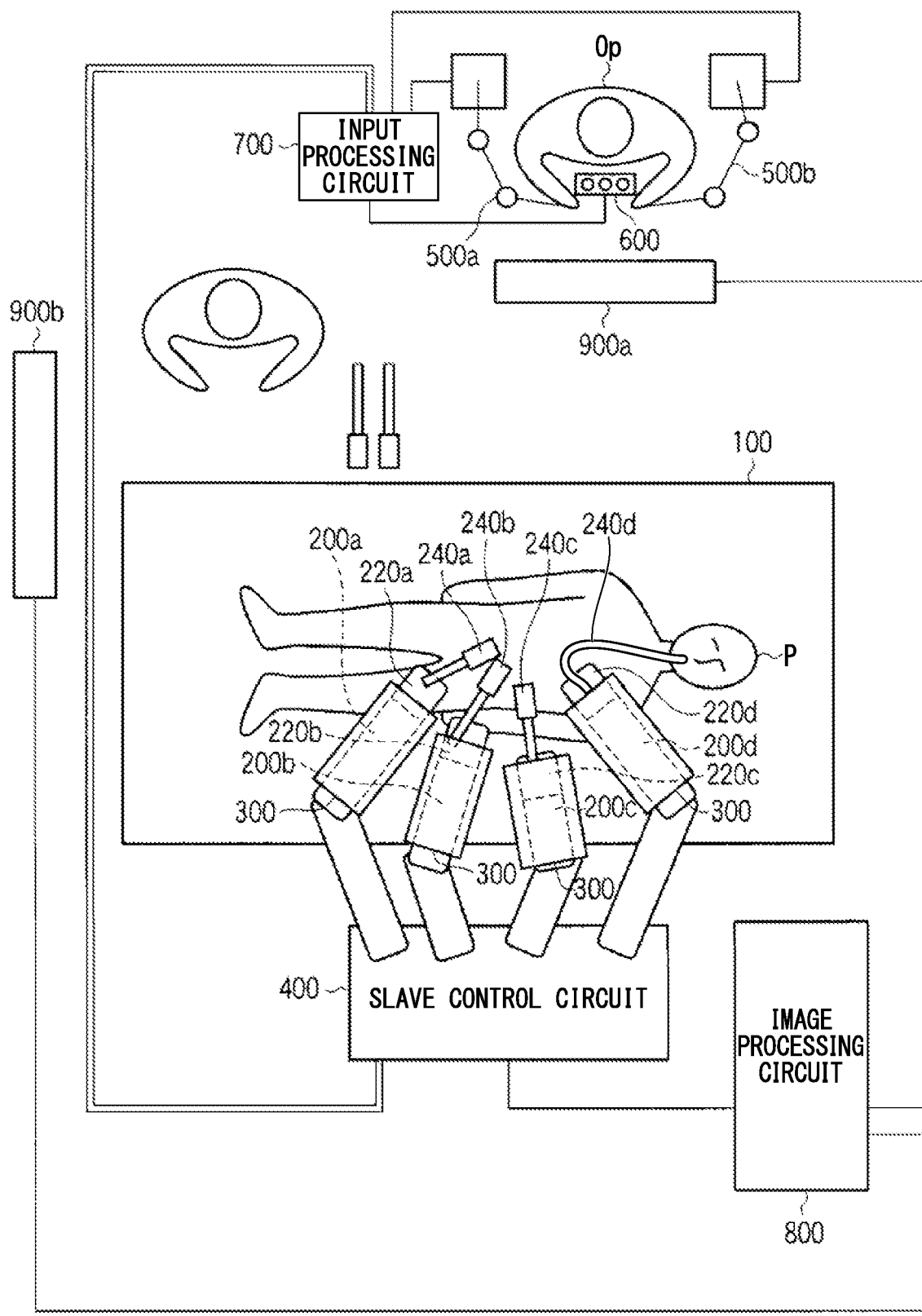
FIG. 1 is a schematic view showing an example of the configuration of a medical manipulator system to which a medical manipulator of the present invention is applied.

Hereinafter, embodiments of the present invention will be described with reference to the accompanying drawings. In all the drawings, even in the case of different embodiments, members that are the same as or equivalent to members described in previous embodiments will be designated by the same reference numerals, and common description will be omitted here.

First Embodiment

Hereinafter, although a first embodiment of the present invention will be described, an example of a medical manipulator system to which a medical manipulator of the present embodiment is applied will be described before the description of the first embodiment.

FIG. 1 is a schematic view showing the example of the configuration of the medical manipulator system to which the medical manipulator of the present invention is applied.

An example of a master slave type medical manipulator system is shown in FIG. 1. The master slave type medical manipulator system is a system that has two types of arms including a master arm and a slave arm and that remotely controls the slave arm so as to follow the operation of the master arm. As a configuration in which a surgical tool is mounted on this slave arm, the medical manipulator of the present invention can be applied.

The medical manipulator system shown in FIG. 1 has an operating table 100, slave arms 200a, 200b, 200c, and 200d, a slave control circuit 400, master arms 500a and 500b, an operating unit 600, an input processing circuit 700, an image processing circuit 800, an operator display 900a, and an assistant display 900b.

Hereinafter, in order to simplify description, symbols "Xa, Xb, . . . , Xz" in alphabetical order may be expressed as "Xa to Xz". For example, the "slave arms 200a, 200b, 200c, and 200d" may be expressed as the "slave arms 200a to 200d".

The operating table 100 is a bed on which a patient P who is a target to be observed and treated is placed. The plurality of slave arms 200a to 200d are installed in the vicinity of the operating table 100. In addition, the slave arms 200a to 200d may be installed at the operating table 100.

The respective slave arms 200a to 200d are configured to have a plurality of multiple degree-of-freedom joints, respectively, and surgical tools or the like mounted on distal end sides (referred to as a side directed to a body cavity of the patient P) of the slave arms 200a to 200d are positioned with respect to the patient P placed on the operating table 100 by bending the respective multiple degree-of-freedom joints. The respective multiple degree-of-freedom joints are individually driven by a power unit that is not shown. As the power unit, for example, a motor (servo motor) having a servo mechanism including an incremental encoder, a decelerator, or the like, can be used, and the operation control of the motor is performed by the slave control circuit 400.

The slave arms 200a to 200d also have a plurality of power units for driving mounted surgical tools 240a to 240d (not shown). Servo motors, for example, can also be used as these power units, and the operation control thereof is performed by the slave control circuit 400.

When the power units of the slave arms 200a to 200d are driven, the driving amounts of the power units are detected by position detectors. Detection signals from the position detectors are input to the slave control circuit 400, and the driving amounts of the slave arms 200a to 200d are detected in the slave control circuit 400 by the detection signals.

Surgical power transmission adapters (hereinafter simply referred to as "adapters") 220a, 220b, 220c, and 220d are interposed between the slave arms 200a to 200d and the surgical tools 240a to 240d, and connect the slave arms 200a to 200d and the surgical tools 240a to 240d, respectively. The adapters 220a to 220d have drive mechanisms that drive the surgical tools 240a to 240d, respectively, and are configured so that power generated in the power unit of a corresponding slave arm is transmitted to a corresponding surgical tool.

For example, linear motion mechanisms, turning mechanisms, or the like are provided with the drive mechanisms of the adapters 220a to 220d according to the configuration of the corresponding surgical tools.

The surgical tools 240a to 240d may be rigid or may be flexible. That is, as the surgical tools 240a to 240d, a surgical tool that operates an effector for performing a treatment on a living body by pushing and pulling of a rigid rod, and a surgical tool that operates an effector for performing a treatment on a living body by pulling of flexible wires can be appropriately selected and adopted. An example is shown in FIG. 1. The surgical tools 240a to 240c are rigid and the surgical tool 240d is flexible. The flexible surgical tool is introduced from a natural opening of a patient, such as a mouth, via an alimentary canal or the like to the inside of the body.

The slave control circuit 400 is configured to have, for example, a CPU, a memory, or the like. The slave control circuit 400 stores a predetermined program for performing the control of the slave arms 200a to 200d, and controls the operation of the slave arms 200a to 200d or the surgical tools 240a to 240d according to control signals from the input processing circuit 700. That is, the slave control circuit 400 specifies a slave arm (or a surgical tool), which is an operation target of a master arm operated by an operator Op, on the basis of a control signal from the input processing circuit 700, and calculates a driving amount required in order to cause the specified slave arm or the like to perform a movement corresponding to the operation amount of the master arm by the operator Op.

Also, the slave control circuit 400 controls the operation of the slave arm or the like that is the operation target of the master arm according to the calculated driving amount. In this case, the slave control circuit 400 inputs a driving signal to the corresponding slave arm, and controls the magnitude and polarity of the driving signal according to a detection signal input from a position detector of a power unit according to the operation of the corresponding slave arm so that the driving amount of the slave arm that is the operation target becomes a target driving amount.

The master arms 500a and 500b is configured by a plurality of link mechanisms. Respective links that constitute the link mechanisms are provided with, for example, position detectors, such as incremental encoders. By detecting the operation of the respective links with the position detectors, the operation amounts of the master arms 500a and 500b are detected in the input processing circuit 700.

The medical manipulator system of FIG. 1 operates the four slave arms using the two master arms 500a and 500b. In the medical manipulator system, it is necessary to appropriately switch the slave arms that are operation targets of the master arms. Such switching is performed, for example, by the operation of the operating unit 600 by the operator Op. Of course, if the operation targets have one-to-one correspondence by causing the number of the master arms and the number of the slave arms to be the same number, such switching is unnecessary.

The operating unit 600 has various operating members, such as switching buttons for switching the slave arms that are the operation targets of the master arms 500a and 500b, a scaling changing switch that changes the operation ratio of the master arms and the slave arms, and a foot switch for emergency-stopping of the system. When a certain operating member that constitutes the operating unit 600 is operated by the operator Op, an operation signal according to the operation of the corresponding operating member is input from the operating unit 600 to the input processing circuit 700.

The input processing circuit 700 analyzes operation signals from master arms 500a and 500b and operation signals from the operating unit 600, and generates control signals for controlling the medical manipulator system according to analysis results of the operation signals to input the control signals to the slave control circuit 400.

The image processing circuit 800 performs various kinds of image processing for displaying image signals input from the slave control circuit 400, to generate display image data in the operator display 900a and the assistant display 900b. The operator display 900a and the assistant display 900b include, for example, liquid crystal displays, and display images on the basis of the image data generated in the image processing circuit 800 according to image signals acquired via an observation instrument.

In the medical manipulator system configured as described above, if the operator Op operates the master arms 500a and 500b, the corresponding slave arms and the surgical tools attached to the slave arms operate in correspondence with the movement of the master arms 500a and 500b. Accordingly, a desired procedure can be performed on the patient P.

Next, the medical manipulator of the present embodiment will be described.

Figure 2:
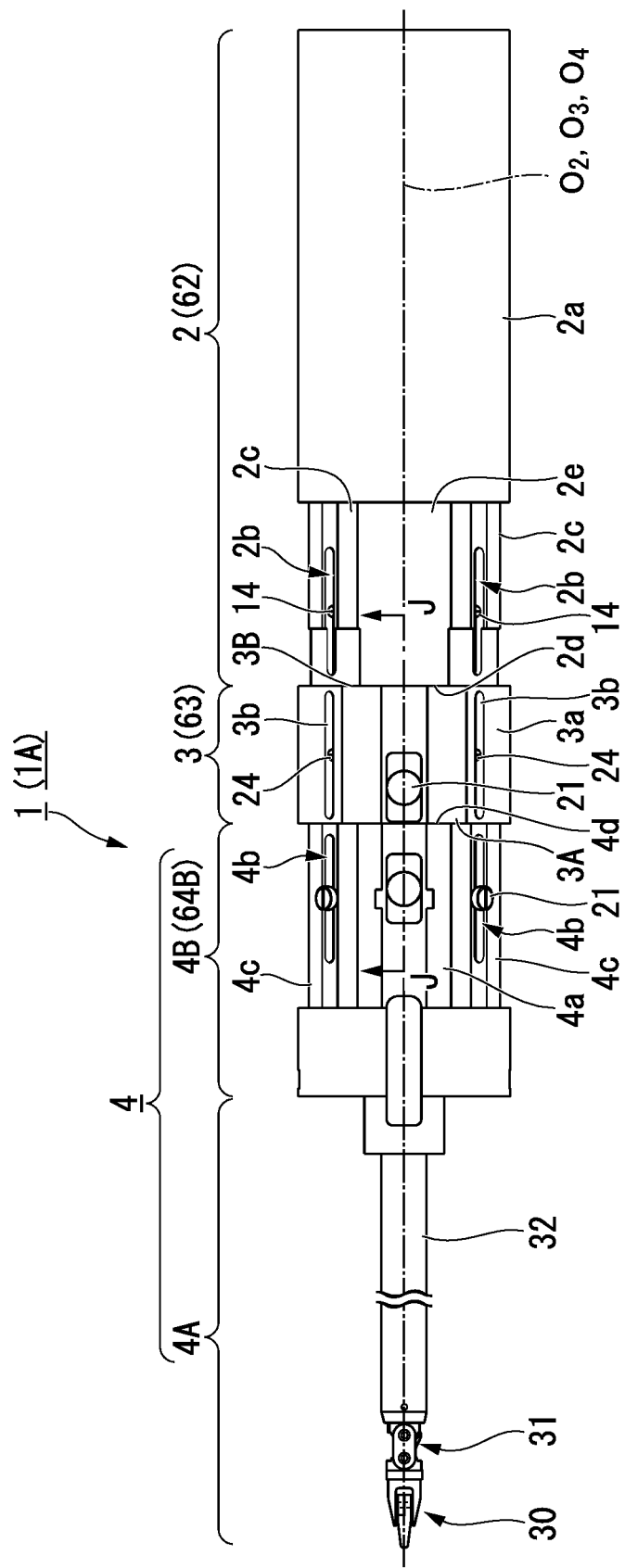
FIG. 2 is a schematic plan view showing the configuration of a medical manipulator of a first embodiment of the present invention.
Figure 3:
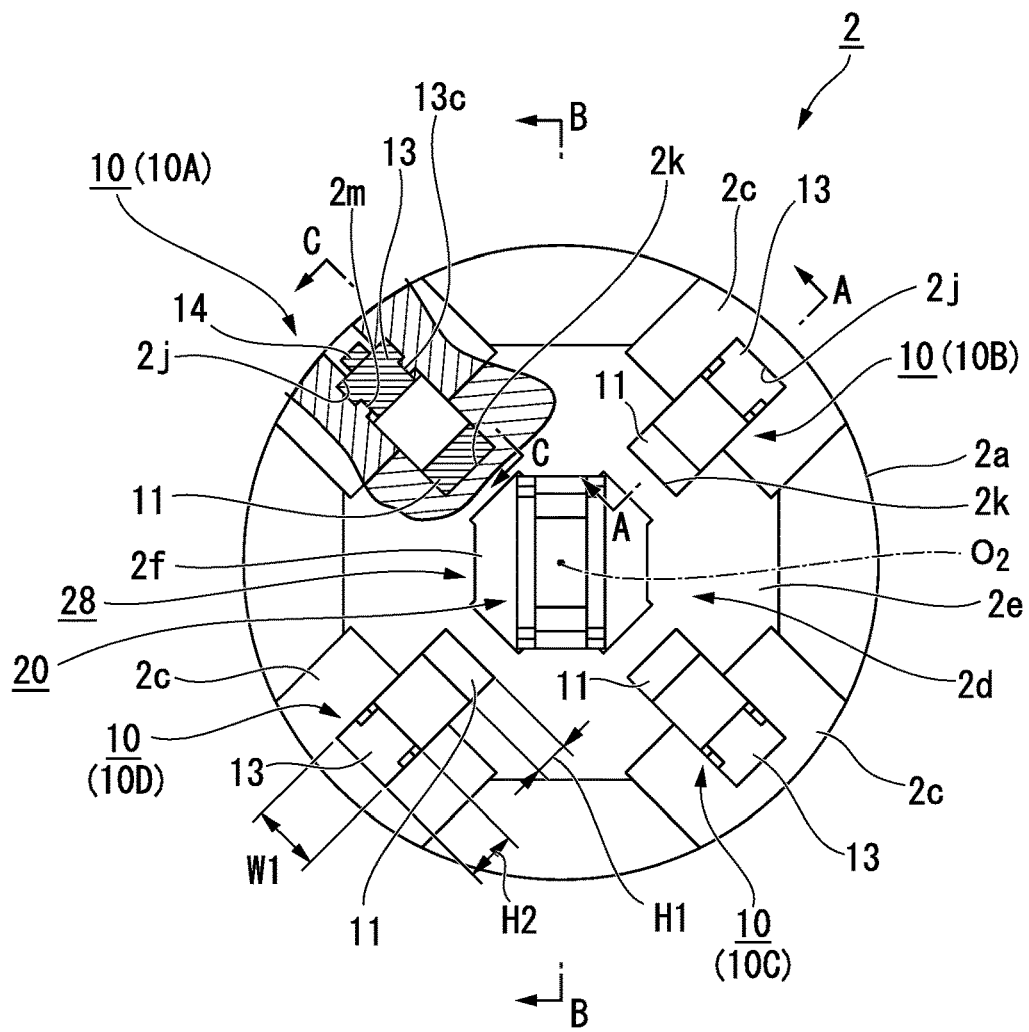
FIG. 3 is a schematic side view on a distal end side of a surgical tool drive unit of the medical manipulator of the first embodiment of the present invention.
Figure 4:
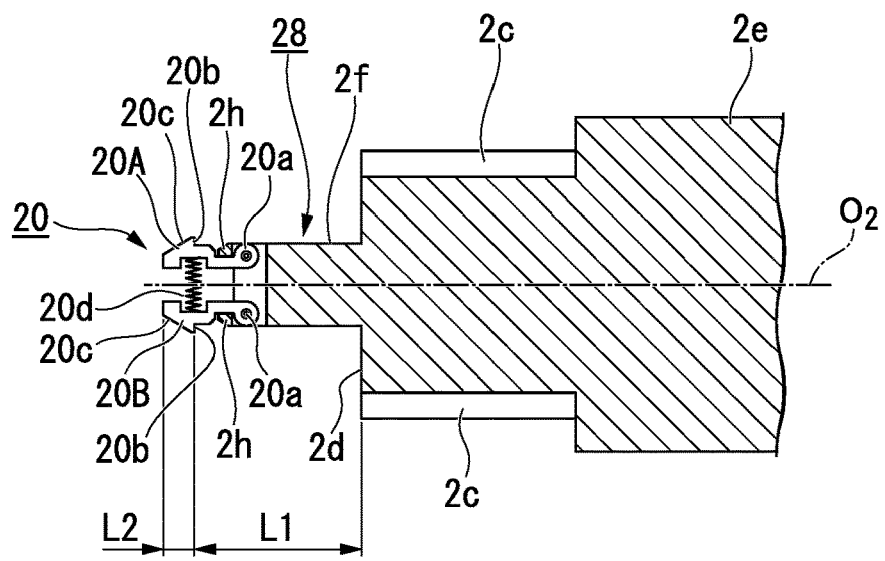
FIG. 4 is a cross-sectional view taken along line B-B in FIG. 3.
Figure 5:
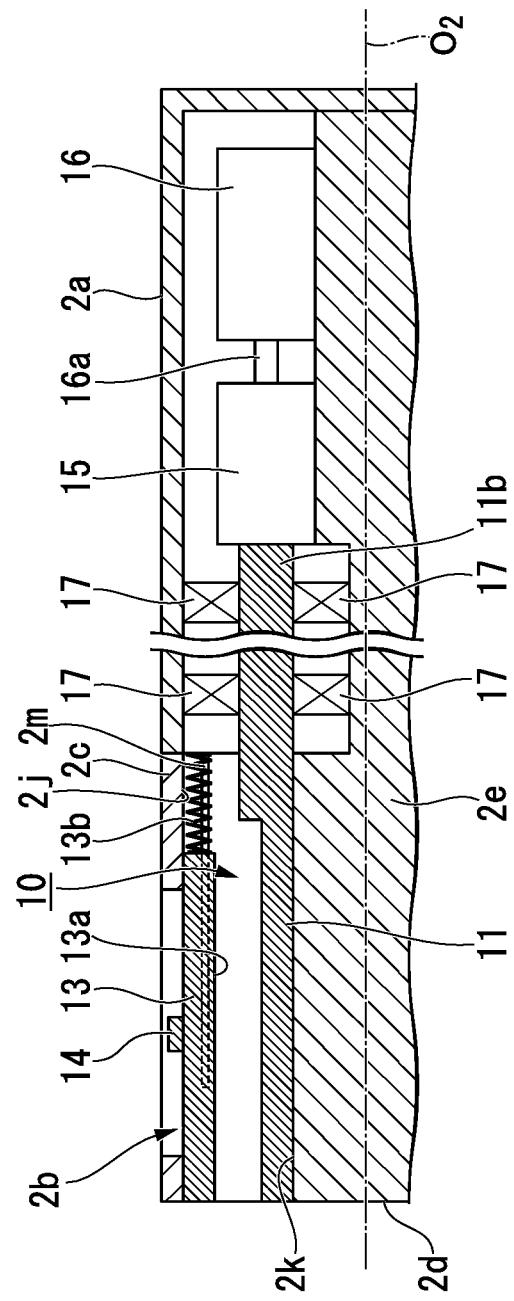
FIG. 5 is a cross-sectional view taken along line A-A in FIG. 3.
Figure 6:
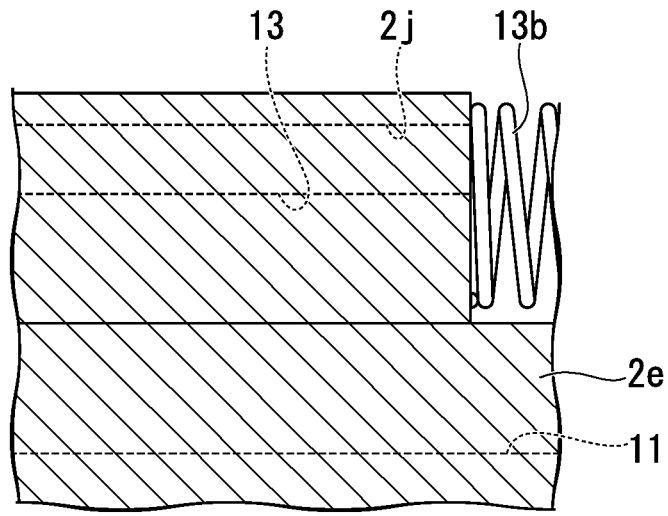
FIG. 6 is a cross-sectional view taken along line C-C in FIG. 3.
Figure 7:
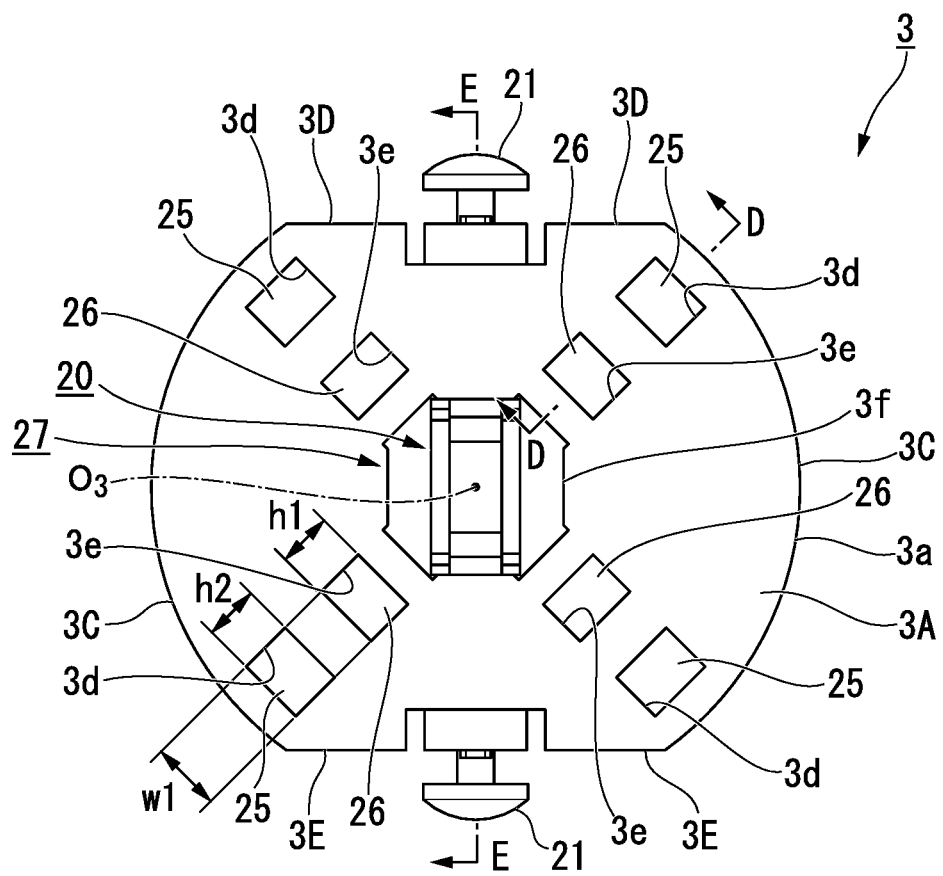
FIG. 7 is a schematic side view on a distal end side of an intermediate member of the medical manipulator of the first embodiment of the present invention.
Figure 8:
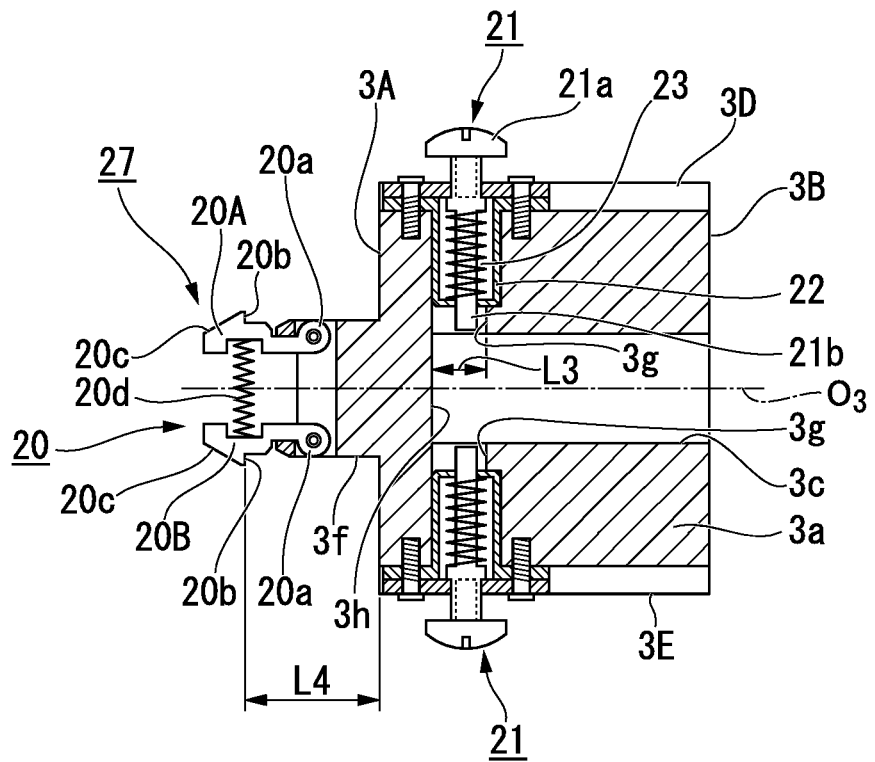
FIG. 8 is a cross-sectional view taken along line E-E in FIG. 7.
Figure 9:
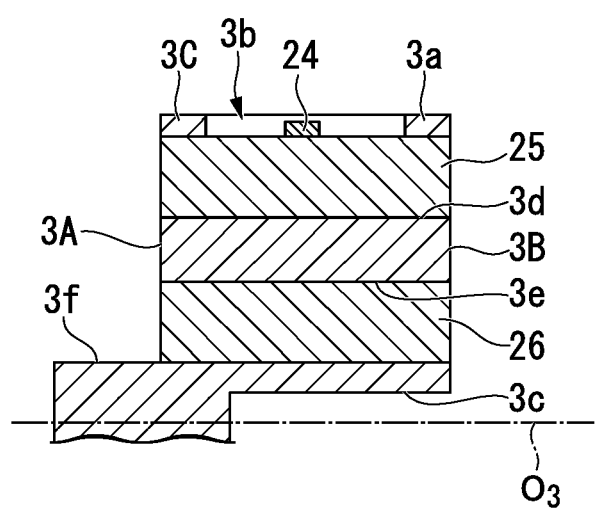
FIG. 9 is a cross-sectional view taken along line D-D in FIG. 7.
Figure 10:
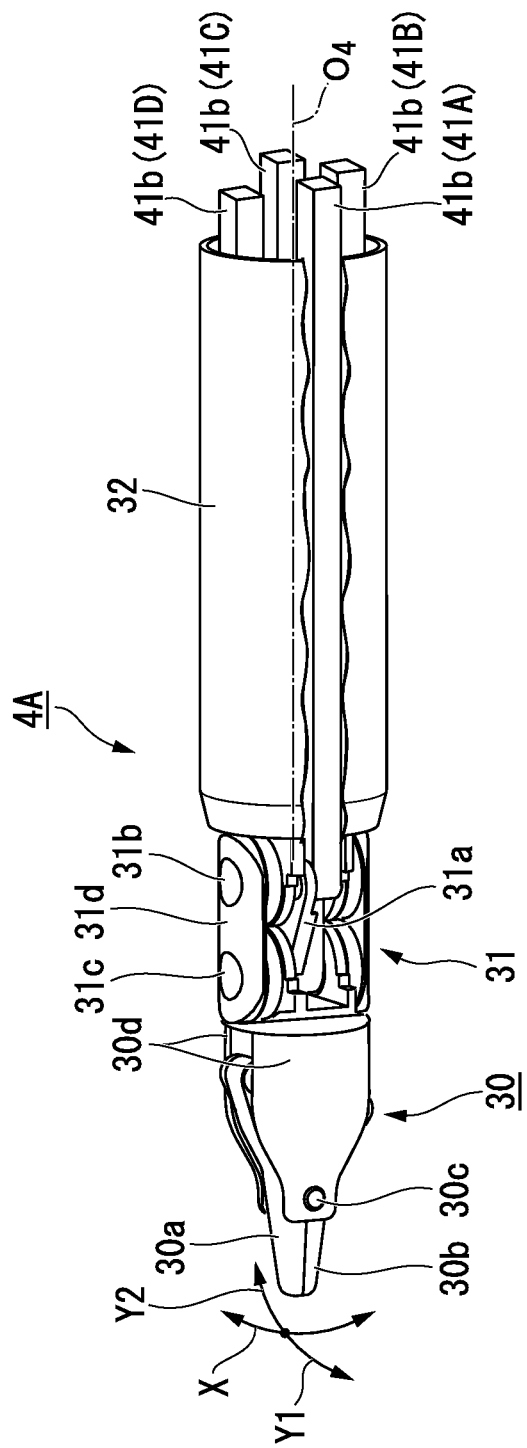
FIG. 10 is a schematic perspective view of a surgical tool unit of the medical manipulator of the first embodiment of the present invention.
Figure 11:
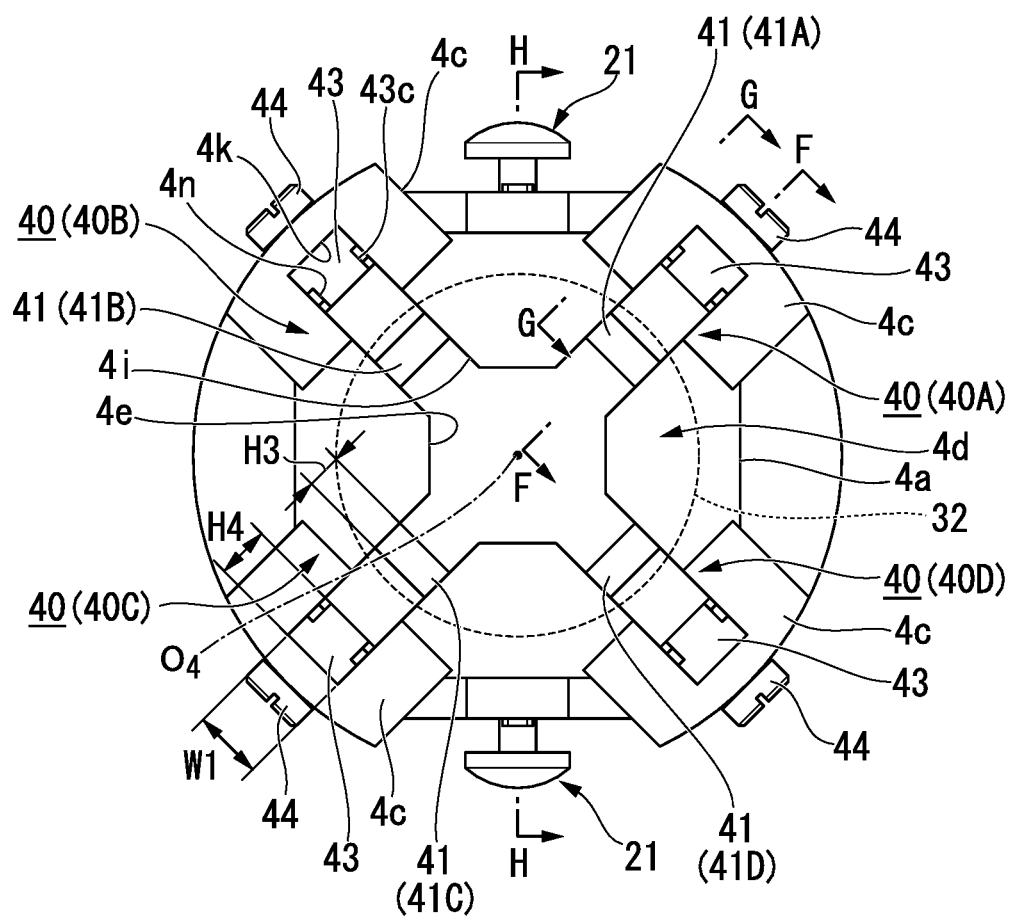
FIG. 11 is a schematic side view on a proximal end side of the surgical tool unit of the medical manipulator of the first embodiment of the present invention.
Figure 12:
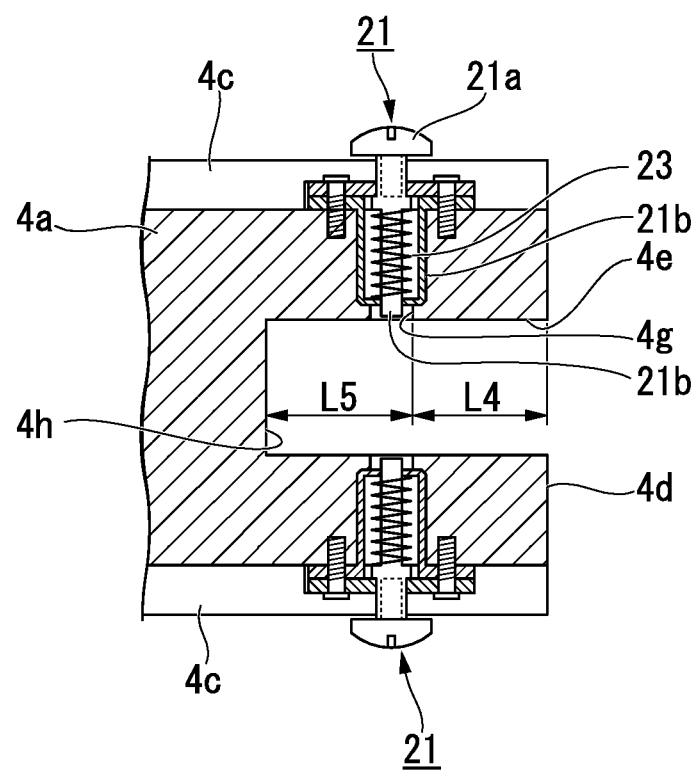
FIG. 12 is a cross-sectional view taken along line H-H in FIG. 11.
Figure 13A:
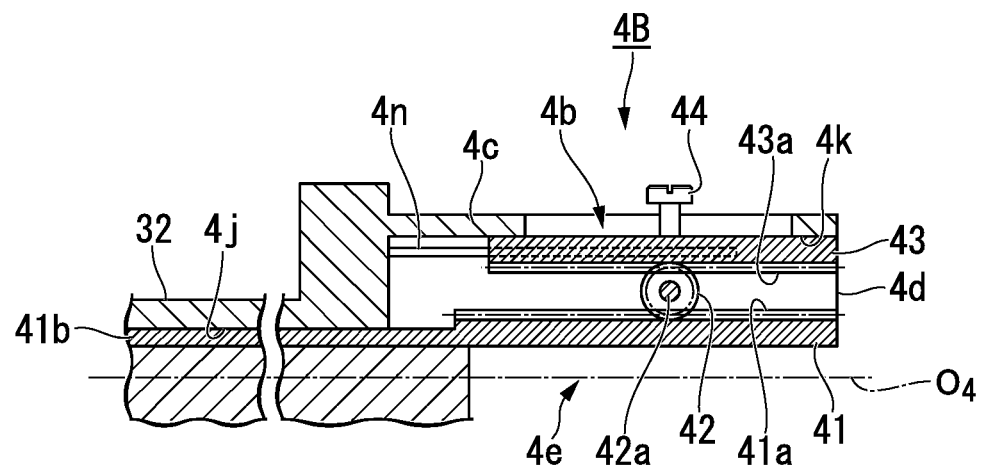
FIG. 13A is a cross-sectional view taken along line F-F in FIG. 11.
Figure 13B:
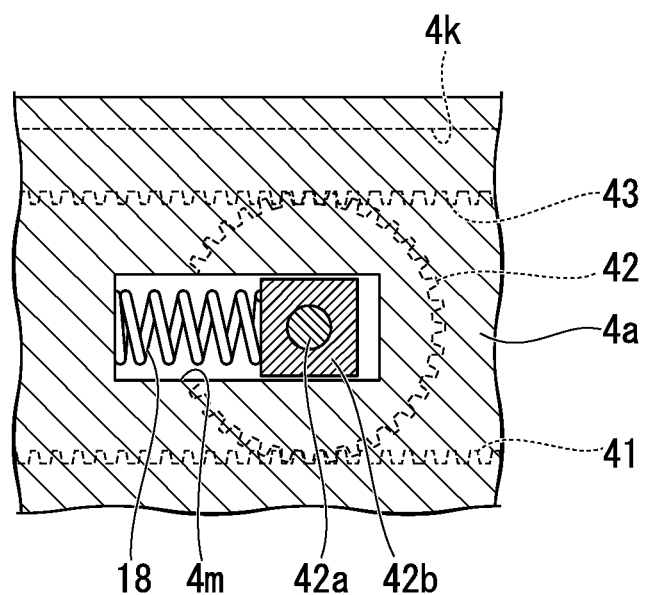
FIG. 13B is a cross-sectional view taken along line G-G in FIG. 11.
Figure 14:
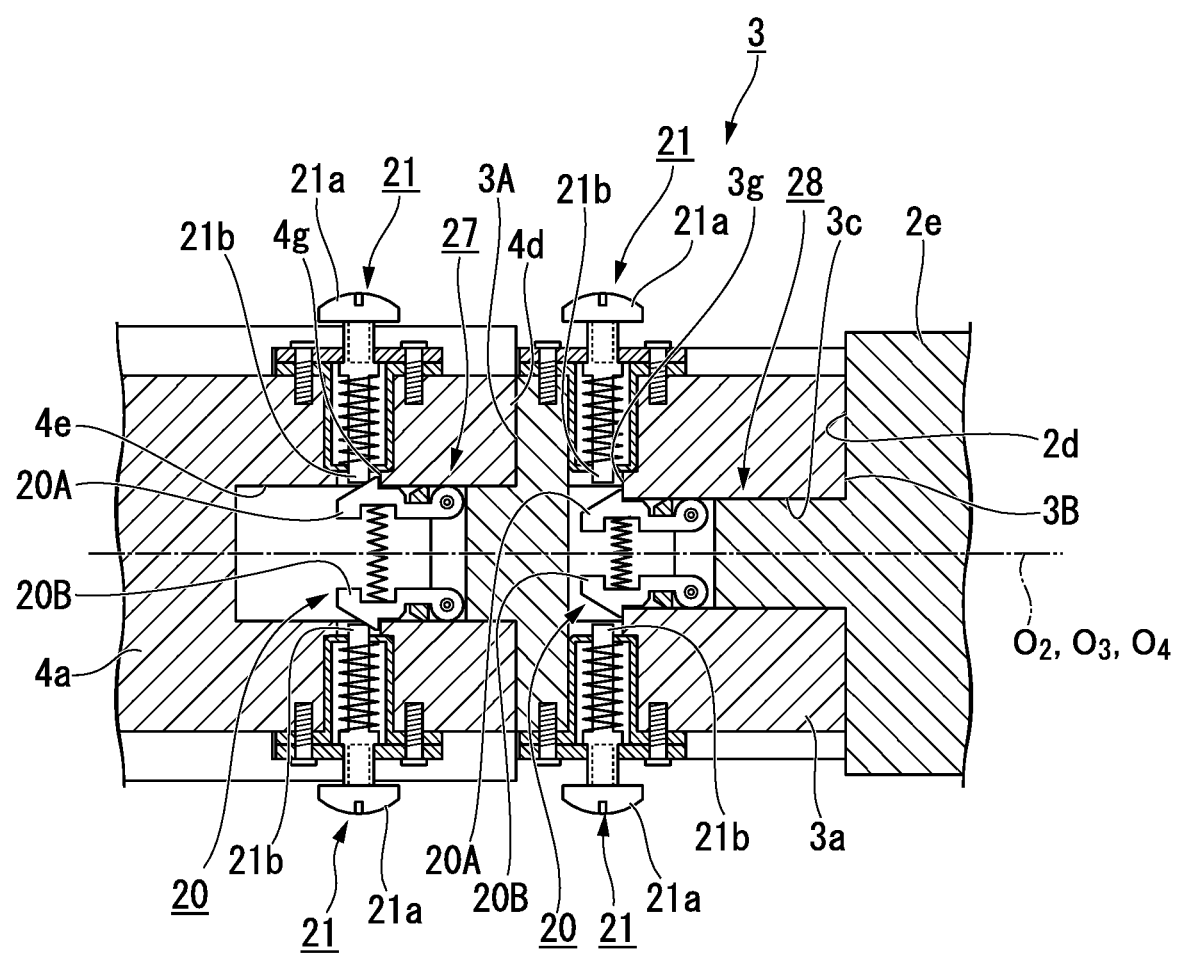
FIG. 14 is a cross-sectional view taken along line J-J in FIG. 2.

FIG. 2 is a schematic plan view showing the configuration of the medical manipulator of the first embodiment of the present invention. FIG. 3 is a schematic side view on a distal end side of a surgical tool drive unit of the medical manipulator of the first embodiment of the present invention. FIG. 4 is a cross-sectional view taken along line B-B in FIG. 3. FIG. 5 is a cross-sectional view taken along line A-A in FIG. 3. FIG. 6 is a cross-sectional view taken along line C-C in FIG. 3. FIG. 7 is a schematic side view on a distal end side of an intermediate member of the medical manipulator of the first embodiment of the present invention. FIGS. 8 and 9 are a cross-sectional view taken along line E-E and a cross-sectional view taken along line D-D in FIG. 7, respectively. FIG. 10 is a schematic perspective view of the surgical tool unit of the medical manipulator of the first embodiment of the present invention. FIG. 11 is a schematic side view on a proximal end side of the surgical tool unit of the medical manipulator of the first embodiment of the present invention. FIG. 12 is a cross-sectional view taken along line H-H in FIG. 11. FIG. 13A is a cross-sectional view taken along line F-F in FIG. 11. FIG. 13B is a cross-sectional view taken along line G-G in FIG. 11. FIG. 14 is a cross-sectional view taken along line J-J in FIG. 2. FIG. 15 is a schematic configuration view of main portions of the medical manipulator of the first embodiment of the present invention.

The medical manipulator 1 of the present embodiment shown in FIG. 2 is a manipulator that can be used instead of the slave arms with a surgical tool in the above medical manipulator system.

The medical manipulator 1 may include the same joint and arm structure as proximal end sides of the above slave arms at a proximal end portion thereof and may be configured to replace the above whole slave arms. However, an example of a configuration in which a portion closer to a distal end side than a joint of the slave arm 200*a* is replaced with the medical manipulator will be described below as an example.

That is, the medical manipulator 1 described below can replace the overall configuration of the above slave arms by being detachably provided at a distal end portion of a joint arm supporting mechanism (not shown) that has the same joint and arm structure as the proximal end side of the above slave arm.

In this way, the medical manipulator 1 can be mounted instead of the above surgical tool 240*a*, adapter 220*a*, and slave arm 200*a*, in the above medical manipulator system. Additionally, the medical manipulator of the present embodiment can also be mounted instead of the flexible surgical tool 240*d*, the adapter 220*d*, and the slave arm 200*d*.

The medical manipulator 1, for example, includes a surgical tool drive unit 2 corresponding to the portion on the distal end side of the slave arm 200*a*, an intermediate member 3 corresponding to the adapter 220*a*, and a surgical tool unit 4 corresponding to the surgical tool 240*a*.

In the following, when the relative positional relationship along the longitudinal direction of the medical manipulator 1 is expressed, unless particularly mentioned, similar to the above, a side directed to the body cavity of the patient's P at the time of use is referred to as a distal end side and the opposite side thereof is referred to as a proximal end side.

The surgical tool drive unit 2 is provided on the proximal end side of the medical manipulator 1, and has a substantially shaft-shaped outer shape that extends from the proximal end side to the distal end side as a whole.

Additionally, the surgical tool drive unit 2 includes a proximal portion 2*e*, which is detachably coupled to the proximal end side of the intermediate member 3, on the distal end side thereof, and includes a housing 2*a*, which forms a columnar outer shape, on the proximal end side thereof.

Synthetic resin or metal, for example, can be used as the material of the proximal portion 2*e* and the housing 2*a*.

A coupling end surface 2*d* that abuts against a coupling end surface 3B on the proximal end side of the intermediate member 3 to be described below is formed on the distal end side of the proximal portion 2*e*.

In the present embodiment, as shown in FIG. 3, the outer shape of the proximal portion 2*e* is an octagonal prismatic shape that has an outer shape smaller than the outer shape of the housing 2*a* at a position that is coaxial with a central axis O2 of the housing 2*a*. As shown in FIG. 4, a coupling protrusion 28 for coupling with the intermediate member 3 is provided at a central portion of the coupling end surface 2*d* so as to protrude toward the distal end side.

In the following, for the purpose of simplicity, a direction along a central axis (defined by the central axis O2 of the housing in the present embodiment) of the surgical tool drive unit 2 may referred to as an axial direction, a direction intersecting the central axis within a plane orthogonal to the central axis may be referred to as a radial direction, and a circumferential direction of a circle centered on the central axis in the plane orthogonal to the central axis may be referred to as a circumferential direction. Additionally, when far and near relative positions in the radial direction with respect to the central axis are expressed, terms, such as an outer peripheral side or a radial outer side and an inner peripheral side or a radial inner side, may be used.

Additionally, when there is no concern of misunderstanding, the same terms may be also used regarding other shaft-shaped members in which the central axis is clear (also including substantially shaft-shaped members).

The coupling protrusion 28 includes an octagonal prismatic engaging projection portion 2*f* that extends along the axial direction from the coupling end surface 2*d* to the distal end side, and an engaging portion 20 that is provided on the distal end side of the engaging projection portion 2*f*.

The engaging portion 20 includes engaging arm portions 20A and 20B that are rotatably fixed by a rotation fulcrum 20*a* and are provided to face each other, and a coil spring 20*d*.

Both of the engaging arm portions 20A and 20B extend to the distal end side of the engaging projection portion 2*f* along an extending direction of the engaging projection portion 2*f*, and are inserted between a pair of stoppers 2*h* provided at the distal end of the engaging projection portion 2*f*.

The coil spring 20*d* is an elastic member that is arranged between distal end portions of the engaging arm portions 20A and 20B and biases the engaging arm portions 20A and 20B to the outsides in respective facing directions. For this reason, the engaging arm portions 20A and 20B are biased toward the outsides of lateral surfaces of the engaging projection portion 2*f* around the respective rotation fulcrums 20*a* by the coil spring 20*d*, and are pressed against the insides of the stoppers 2*h*.

The shapes of the distal end portions of the engaging arm portions 20A and 20B are formed as flat portions that are aligned with the lateral surfaces of the engaging projection portion 2*f* in a state where the engaging arm portions are pressed against the stoppers 2*h*. Engaging claw portions 20*b* that are step portions that protrude toward the outsides of the lateral surfaces of the engaging projection portion 2*f* are formed at the distal ends of the flat portions.

The position of each engaging claw portion 20*b* in the axial direction is set to a position that has a distance L1 from the coupling end surface 2*d* in a state where the engaging arm portions 20A and 20B are pressed against the stoppers 2*h*.

An inclination portion 20*c* that inclines in a direction directed to the central axis O2 extends within a range of distance L2 on the distal end side from a top portion of the engaging claw portion 20*b* in a protruding direction. The width between the distal ends of the respective inclination portions 20*c* is smaller than the width of the engaging projection portion 2*f*.

Additionally, as shown in FIG. 3, a second input member housing portion 2*c* that houses a second input member 13 to be described below therein is provided on the outer peripheral side of the proximal portion 2*e* so as to protrude to the radial outer side. In the present embodiment, a total of four second input member housing portions 2*c* are provided on alternate lateral surfaces of the octagonal prismatic proximal portion 2*e*.

The outer shape of each second input member housing portion 2*c* in the radial direction is aligned with the cylindrical outer shape of the housing 2*a*.

A reciprocation drive unit 10 is provided for every second input member housing portion 2*c* inside the proximal portion 2*e* and each second input member housing portion 2*c*. Although the configurations of the respective reciprocation drive units 10 are the same in the present embodiment, when the reciprocation drive units are each distinguished from each other, the respective drive units may be referred to as reciprocation drive units 10A, 10B, 10C, and 10D in the clockwise direction shown in FIG. 3.

The reciprocation drive unit 10, as shown in FIG. 5, includes a first input member 11 (one of a pair of input members), a linear motion converter 15 (drive source), a motor 16 (drive source), a second input member 13 (the other of a pair of the input members), and biasing member 13b (drive-unit-side biasing member).

The first input member 11 is a rod-shaped member that advances and retracts in a direction along the central axis O2 toward the intermediate member 3 coupled in the coupling end surface 2d, and transmits a driving force at the time of advance. In the present embodiment, the first input member 11 is bar-shaped as a whole, and has a cross-sectional shape of width W1×thickness H1.

As the material of the first input member 11, a material including proper rigidity in order to transmit a driving force is preferable; for example, metal can be used.

The portion of the first input member 11 on the distal end side is housed in a guide groove 2k that slidably holds the first input member 11.

The guide groove 2k is a groove portion that extends to penetrate in the axial direction parallel to the central axis O2 in the portion of the proximal portion 2e located further toward the outer peripheral side than the engaging projection portion 2f.

Additionally, the portion of the first input member 11 on the proximal end side extends to the inside of the housing 2a, and is supported by a plurality of sliding bearings 17 arranged inside the housing 2a so as to be capable of advancing and retracting.

The linear motion converter 15 and the motor 16 constitute the drive source that advances and retracts the first input member 11 in the direction along the central axis O2, and are fixed within the housing 2a.

The linear motion converter 15 is provided between the end portion of the first input member 11 nearest to the proximal end side, and a rotating shaft 16a of the motor 16, and converts the rotary motion of the motor 16 into a linear motion in the direction along the central axis O2.

Although the configuration of the linear motion converter 15 is not particularly limited if a rotary motion can be converted into a linear motion, a feed-screw mechanism is adopted as an example in the present embodiment.

The motor 16 is electrically connected to the slave control circuit 400, and changes the rotational direction and rotational angle of the rotating shaft 16a according to a control signal from the slave control circuit 400. As the motor 16, for example, a DC motor or the like can be adopted.

The second input member 13 is a rod-shaped member that advances and retracts in the direction along the central axis O2 toward the intermediate member 3 coupled in the coupling end surface 2d, and transmits a driving force at the time of advance. In the present embodiment, the second input member 13 is substantially bar-shaped as a whole, and has a cross-sectional shape of width W1×thickness H2.

As the material of the second input member 13, a material including proper rigidity in order to transmit a driving force is preferable; for example, metal can be used.

A slip-out preventing pin 14 that regulates the advancing and retracting amounts of the second input member 13 is provided so as to protrude from a lateral surface of the second input member 13.

The second input member 13 having such a configuration is housed in a guide groove 2j that slidably holds the second input member 13.

The biasing member 13b that biases the second input member 13 to the distal end side is provided on the proximal end side of the second input member 13. In the present embodiment, the biasing member 13b is a compression coil spring that couples a proximal end of the second input member 13 and the second input member housing portion 2c together and that expands and contracts in advance and retract directions of the second input member 13.

The guide groove 2j is a groove portion that extends to penetrate in the direction along the central axis O2 inside the second input member housing portion 2c, and has a groove bottom surface that slides on the lateral surface of the second input member 13.

In the groove bottom surface of the guide groove 2j, a long-hole-shaped stopper groove 2b penetrates along the longitudinal direction of the guide groove. The slip-out preventing pin 14 of the second input member 13 is inserted through the inside of the stopper groove 2b.

For this reason, a range where the second input member 13 can advance and retract is regulated by the opening amount of the stopper groove 2b in the longitudinal direction.

A protrusion 2m that protrudes toward the second input member 13 is provided on a groove lateral surface of the guide groove 2j except for the distal end side of the guide groove 2j. A range where the protrusion 2m is not provided is a range where a second intermediate transmission member 25 to be described below can advance from the coupling end surface 2d.

Meanwhile, the lateral surface of the second input member 13 is provided with a step portion 13c that engages the protrusion 2m, and thereby, the lateral surface of the second input member 13 is configured so as to be capable of coming into close contact with and sliding on the groove bottom surface of the guide groove 2j when the second input member 13 advances and retracts.

The guide grooves 2k and 2j may include two separate rectangular guide holes adapted to the outer shapes of the first input member 11 and the second input member 13, respectively. In the present embodiment, however, the guide grooves are constituted by rectangular holes that communicate with each other in the radial direction and are long in the radial direction as a whole. That is, the guide groove 2k is formed at the end portion of the rectangular hole on the radial inner side, and the guide groove 2j is formed at the end portion of the rectangular hole on the radial outer side.

For this reason, rod-shaped members having a larger cross-sectional area than the first input member 11 and the second input member 13 can be inserted into the guide grooves 2k and 2j if the rod-shaped members have a width that is equal to or less than the width W1 of the guide grooves in the circumferential direction.

In the present embodiment, two sets of reciprocation drive units 10 having such a configuration, as shown in FIG. 3, are provided so as to face each other, respectively, in biaxial directions orthogonal to the central axis O2. Additionally, even in any reciprocation drive unit 10, the first input member 11 is arranged on the center side of the coupling end surface 2d compared to the second input member 13. Additionally, when a direction in which the first input member 11 and the second input member 13 are coupled together in the coupling end surface 2d is defined as an arrangement direction of the reciprocation drive unit 10, the respective reciprocation drive units 10 are radially arranged around the central axis O2.

The intermediate member 3 is a member that detachably couples the surgical tool drive unit 2 and the surgical tool unit 4 together and that transmits a driving force from the surgical tool drive unit 2 to the surgical tool unit 4 side.

The schematic configuration of the intermediate member 3, as shown in FIG. 7, includes an intermediate member body 3a, a first intermediate transmission member 26, and a second intermediate transmission member 25.

The intermediate member body 3a includes, at both ends thereof, a coupling end surface 3B (drive-unit-side end portion) that comes into close contact with and abuts against the coupling end surface 2d of the surgical tool drive unit 2, and a coupling end surface 3A (surgical-tool-unit-side end portion) that is arranged parallel to the coupling end surface 3B and comes into close contact with and abuts against a coupling end surface 4d (to be described below) of the surgical tool unit 4.

The schematic shape of the intermediate member body 3a in a side view has a shape such that a circle aligned at the housing 2a is cut out by two parallel lines. This shape is a substantially shaft-shaped member that extends along a central axis O3 that is a straight line that passes through the centerline of the circle aligned at the housing 2a. For this reason, the intermediate member body 3a includes curved lateral surfaces 3C that are curved in a circular-arc shape, and a planar lateral surfaces 3D and 3E including planes.

The engaging projection portion 2f of the surgical tool drive unit 2 is inserted into a central portion of the coupling end surface 3B, and an engaging hole 3c that fixes the position of the surgical tool drive unit 2 in the radial direction with respect to the intermediate member 3, as shown in FIG. 8, extends along the central axis O3.

A locking surface 3g that extends toward the outside of the engaging hole 3c is provided at a position with a distance L1 from the coupling end surface 3B inside the engaging hole 3c. A hole back surface 3h of the engaging hole 3c is located on the distal end side by a distance L3 from the locking surface 3g. The distance L3 is a dimension larger than the length L2 on the distal end side of the engaging claw portion 20b of the engaging portion 20.

By virtue of such a configuration, if the coupling protrusion 28 is inserted into the engaging hole 3c from the proximal end side, a force, which narrows the facing interval between the engaging arm portions 20A and 20B, acts via the respective inclination portions 20c of the engaging arm portions 20A and 20B from the engaging hole 3c, and the coil spring 20d is compressed and inserted into the engaging hole 3c as being pushed into the engaging hole 3c.

When the engaging portion 20 is pushed in further toward the distal end side than the locking surface 3g, each engaging claw portion 20b biased by the coil spring 20d protrudes to the radial outer side and is locked to the locking surface 3g. Accordingly, the surgical tool drive unit 2 is configured so as to be capable of being connected to the intermediate member 3 (refer to FIG. 14).

As shown in FIG. 8, a coupling protrusion 27 for coupling with the surgical tool unit 4 is provided at the central portion of the coupling end surface 3A so as to protrude toward the distal end side.

The coupling protrusion 27 includes an engaging projection portion 3f that has an octagonal prismatic shape which extends along the axial direction from the coupling end surface 3A to the distal end side and that has the same pair of stoppers 2h as those of the engaging projection portion 2f provided on the distal end side thereof, and the same engaging portion 20 as the above on the distal end side of the engaging projection portion 3f.

The outer shape and size of the engaging projection portion 3f may be the same as those of the engaging projection portion 2f. In the present embodiment, however, there is a difference in that a distance L4 from the coupling end surface 3A to the engaging claw portion 20b is shorter than the distance L1 from the coupling end surface 2d in the coupling protrusion 28 to the engaging claw portion 20b.

The facing direction of the engaging projection portion 3f that faces the engaging arm portions 20A and 20B of the engaging portion 20 is a direction that passes through the central axis O3 and is orthogonal to the planar lateral surfaces 3D and 3E.

The planar lateral surfaces 3D and 3E are respectively provided with release buttons 21 that advance and retract in the radial direction between the locking surface 3g and the hole back surface 3h.

The release button 21 is a member in which an operating portion 21a that performs the operation of releasing the coupling with the surgical tool drive unit 2 is provided at one end portion (a first end portion) of a shaft portion 21b. The other end portion (a second end portion) of the shaft portion 21b is inserted toward the center of the intermediate member body 3a, and the operating portion 21a is arranged so as to protrude toward the outside of the planar lateral surface 3D (3E).

The shaft portion 21b is inserted through the inside of a holder member 22 inserted into the inside of the intermediate member body 3a, and is biased to the radial outer side of the intermediate member body 3a by a coil spring 23 arranged inside the holder member 22.

The length of the shaft portion 21b is set to such a length that the other end portion of the shaft portion 21b withdraws from an inner peripheral surface of the engaging hole 3c to the radial outer side when an external force does not act on the operating portion 21a, and protrudes from the inner peripheral surface of the engaging hole 3c when the operating portion 21a is pressed and pushed into the inner side of the intermediate member body 3a.

As shown in FIG. 7, four guide holes 3e (first guide portions) and four guide holes 3d (second guide portion) are provided to penetrate in a direction along the central axis O3, between the coupling end surfaces 3A and 3B. The guide holes 3e and 3d are radially arranged around the central axis O3. In the present embodiment, one set is provided along each of two axes that pass through the central axis O3 and are orthogonal to each other.

The guide hole 3e is a through hole formed at a position that faces the distal end surface and guide groove 2k of the first input member 11 of the surgical tool drive unit 2 when the surgical tool drive unit 2 is coupled. In the present embodiment, this guide hole is an angled hole including a rectangular cross-section of width W1×thickness h1. Here, the width is a dimension in the circumferential direction, and the thickness is a dimension in the radial direction. The thickness h1 is set to a dimension that is equal to or greater than the width H1 of the first input member 11.

A bar-shaped first intermediate transmission member 26 having a rectangular cross-section of the same shape as the guide hole 3e is slidably inserted into the guide hole 3e.

The guide hole 3d is a through hole formed at a position that faces a distal end surface of the second input member 13 of the surgical tool drive unit 2 when the surgical tool drive unit 2 is coupled, and is an angled hole including a rectangular cross-section of width W1×thickness h2 in the present embodiment. Here, the width is a dimension in the circumferential direction, and the thickness is a dimension in the radial direction. The thickness h2 is set to a dimension that is equal to or greater than the width H2 of the second input member 13.

The bar-shaped second intermediate transmission member 25 having a rectangular cross-section of the same shape as the guide hole 3d is slidably inserted into the guide hole 3d.

As shown in FIG. 9, a stopper groove 3b that is a long-hole shape and penetrates the guide hole 3d is provided at a central portion of each guide hole 3d in the longitudinal direction between each guide hole 3d and the curved lateral surface 3C. A slip-out preventing pin 24 protruding from one lateral surface of the second intermediate transmission member 25 is inserted through the inside of the stopper groove 3b.

For this reason, the range where the second intermediate transmission member 25 can advance and retract is regulated by the opening amount of the stopper groove 3b in the longitudinal direction.

Additionally, the lengths of the first intermediate transmission member 26 and the second intermediate transmission member 25, as shown in FIG. 9, are equal to the distance between the coupling end surface 3A and the coupling end surface 3B.

Metal or synthetic resin having proper rigidity capable of transmitting a driving force can be used as both of the materials of the first intermediate transmission member 26 and the second intermediate transmission member 25.

The surgical tool unit 4 has an effector that operates an operation target, operates the operation target by a driving force transmitted via the intermediate member 3 from the surgical tool drive unit 2 to drive the effector, and is detachably provided with respect to the coupling end surface 3A of the intermediate member 3.

As the effector of the surgical tool unit 4, a proper effector can be adopted if the effector is capable of being operated by driving forces along one axial direction, which are transmitted by the first intermediate transmission member 26 and the second intermediate transmission member 25 that advance and retract with respect to the surgical tool unit 4.

In the following, a case where the surgical tool unit 4 is grip forceps and the effector has a forceps portion and a joint will be described as an example.

The schematic configuration of the surgical tool unit 4, as shown in FIG. 2, is a substantially shaft-shaped body as a whole, and includes a surgical tool body 4A and a driving force transmission section 4B from the distal end side along a central axis O4.

The surgical tool body 4A, as shown in FIG. 10, includes a forceps portion 30 (effector), a joint 31 (effector), and a shaft portion 32 from the distal end side.

The forceps portion 30 includes forceps pieces 30a and 30b that rotate around a rotating shaft 30c fixed to a cover member 30d. End portions (not shown) of wires are coupled to proximal end sides of the forceps pieces 30a and 30b, and other end portions of the wires are inserted into the insides of distal end shaft portions 41b, which are respective distal end portions of the first transmission members 41D and 41B, the shaft portion 32, and the joint 31 and are coupled together.

Since the forceps pieces 30a and 30b are coupled to the first transmission members 41D and 41B, respectively, by the wires (not shown), the forceps piece 30a is opened if the first transmission member 41D retracts to the proximal end side, and the forceps piece 30b is opened if the first transmission member 41B is retracted to the proximal end side. In contrast, the forceps piece 30a is closed if the first transmission member 41D is advanced to the distal end side, the forceps piece 30b is closed if the first transmission member 41B is advanced to the distal end side, and the forceps piece 30a and the forceps piece 30b are brought into contact with each other such that the forceps are closed.

Additionally, if the first transmission member 41D is retracted to the proximal end side and the first transmission member 41B is advanced to the distal end side, the forceps pieces 30a and 30b are rotated in a direction of arrow Y2 shown in the drawing. In contrast, if the first transmission member 41D is advanced to the distal end side and the first transmission member 41B is retracted to the proximal end side, the forceps pieces 30a and 30b are rotated in a direction of arrow Y1 shown in the drawing.

The joint 31 rotates the forceps portion 30 in a direction orthogonal to the axial direction of the shaft portion 32. A driven shaft 31c provided at a proximal end portion of the forceps portion 30 and a rotation supporting shaft 31b provided at a distal end portion of the shaft portion 32 are coupled together by a rotating arm 31d.

The end portion of a driving link 31a on the distal end side is coupled to the driven shaft 31c. Additionally, the distal end portion of the first transmission member 41A that is inserted through the inside of the shaft portion 32 is rotatably coupled to the end portion of the driving link 31a on the proximal end side. Additionally, the driving link 31a is also rotatably coupled to the rotation supporting shaft 31b.

For this reason, the driving link 31a rotates the driven shaft 31c around the rotation supporting shaft 31b by the advance and retract of the first transmission member 41A, and the forceps portion 30 is rotated in a direction of arrow X shown in the drawing in conjunction with the driven shaft 31c.

The first transmission member 41C is coupled to the cover member 30d in order to maintain the orientation of the forceps portion 30 by a link (not shown).

The shaft portion 32 is a member that has a columnar outer shape centered on the central axis O4 and that allow the respective distal end shaft portions 41b of the first transmission members 41A, 41B, 41C, and 41D to be described below to be inserted into the inside thereof. A proximal end side of the shaft portion 32 is connected to the driving force transmission section 4B.

The respective distal end shaft portions 41b are arranged at positions where the circumference centered on the central axis O4 of the shaft portion 32 is equally divided into four, and are held by the guide holes 4j (refer to FIG. 13A) or the like so as to be capable of advancing and retracting within the shaft portion 32.

The driving force transmission section 4B, as shown in FIG. 2, includes a proximal portion 4a, which is detachably coupled to the distal end side of the intermediate member 3, on the proximal end side thereof.

The coupling end surface 4d that abuts against the coupling end surface 3A of the intermediate member 3 is formed on the proximal end side of the proximal portion 4a.

In the present embodiment, as shown in FIG. 11, the outer shape of the proximal portion 4a is an octagonal prismatic shape that has an outer shape larger than the outer shape of the shaft portion 32 at a position that is coaxial with the central axis O4. As shown in FIG. 12, an engaging hole 4e for coupling with the coupling protrusion 27 of the intermediate member 3 is provided at a central portion of the coupling end surface 4d so as to extend toward the distal end side.

Additionally, a second transmission member housing portion 4c that houses a second transmission member 43 to be described below therein is provided on the outer peripheral side of the proximal portion 4a so as to protrude to the radial outer side. In the present embodiment, a total of four second transmission member housing portions 4c are provided on alternate lateral surfaces of the octagonal prismatic proximal portion 4a.

The outer shape of each second transmission member housing portion 4c in the radial direction is aligned with the cylindrical outer shape of the curved lateral surface 3C of the intermediate member 3 at the time of coupling.

A locking surface 4g that extends toward the outside of the engaging hole 4e is provided at a position with a distance L4 from the coupling end surface 4d inside the engaging hole 4e. A hole back surface 4h of the engaging hole 4e is located on the distal end side by a distance L5 from the locking surface 4g. The distance L5 is a dimension larger than the length L2 on the distal end side of the engaging claw portion 20b of the engaging portion 20.

By virtue of such a configuration, if the coupling protrusion 27 of the intermediate member 3 is inserted into the engaging hole 4e from the proximal end side, a force, which narrows the facing interval between the engaging arm portions 20A and 20B, acts via the respective inclination portions 20c of the engaging arm portions 20A and 20B from the engaging hole 4e. The coil spring 20d is compressed and the coupling protrusion 27 is inserted into the engaging hole 4e as the coupling protrusion 27 is pushed into the engaging hole 3c.

When the engaging portion 20 is pushed in further toward the distal end side than the locking surface 4g, each engaging claw portion 20b biased by the coil spring 20d protrudes to the radial outer side and is locked to the locking surface 4g. Accordingly, the intermediate member 3 is able to be coupled to the driving force transmission section 4B of the surgical tool unit 4 (refer to FIG. 14).

A pair of lateral surfaces that face each other across the central axis O4 of the proximal portion 4a are respectively provided with the release buttons 21 that advance and retract in the radial direction between the locking surface 4g and the hole back surface 4h.

In the present embodiment, the release buttons 21 have the same configuration as the release buttons provided at the intermediate member 3.

For this reason, the length of the shaft portion 21b is set to such a length that the other end portion of the shaft portion 21b withdraws from an inner peripheral surface of the engaging hole 4e to the radial outer side when an external force does not act on the operating portion 21a, and protrudes from the inner peripheral surface of the engaging hole 4e when the operating portion 21a is pressed and pushed into the inner side of the proximal portion 4a.

As shown in FIG. 11, a reciprocation drive unit 40 is provided for each second transmission member housing portion 4c inside the proximal portion 4a and each second transmission member housing portion 4c. Although the configurations of the respective reciprocation drive units 40 are the same in the present embodiment, when the reciprocation drive units are distinguished from each other, respectively, the respective drive units may be referred to as reciprocation drive units 40A, 40B, 40C, and 40D in the counterclockwise direction shown in FIG. 11.

The reciprocation drive unit 40, as shown in FIG. 13A, includes a first transmission member 41, a second transmission member 43, and a pinion 42.

The first transmission member 41 is a rod-shaped member that moves in the direction along the central axis O4 under a driving force from the first intermediate transmission member 26 at the time of the advance of the first intermediate transmission member 26 of the intermediate member 3 coupled in the coupling end surface 4d and transmits the driving force to the forceps portion 30 or joint 31 that is coupled to the distal end side.

For this reason, each first transmission member 41 is arranged at a position that faces each first intermediate transmission member 26 at the time of the coupling of the intermediate member 3, and is able to advance and retract between the coupling end surface 4d and the coupling end surface 3A in a state where each first transmission members abuts against each facing first intermediate transmission member 26.

In the present embodiment, the first transmission member 41 is bar-shaped as a whole, and has a cross-sectional shape of width W1×thickness H3. However, a rack portion 41a is formed on one lateral surface of the first transmission member 41 on the proximal end side. Additionally, the thickness H3 is set to be equal to or less than the thickness h1 of the first intermediate transmission member 26.

As the material of the first transmission member 41, a material including proper rigidity in order to transmit a driving force is preferable; for example, metal can be used.

A bar-shaped distal end shaft portion 41b having a rectangular cross-section that does not have the rack portion 41a is formed on the distal end side of the first transmission member 41. The distal end shaft portion 41b is inserted through the guide hole 4j of the shaft portion 32 so as to be capable of advancing and retracting.

Additionally, the portion of the first transmission member 41 on the proximal end side where the rack portion 41a is formed and is housed in the guide groove 4i having the width W1 that slidably holds the first transmission member 41, in a state where the rack portion 41a is directed to the radial outer side.

If the reciprocation drive units 40A, 40B, 40C, and 40D are referred to, respectively, in correspondence with the first transmission members 41A, 41B, 41C, and 41D, in the present embodiment, the first transmission members 41B and 41D transmit driving forces to the forceps portion 30, and the first transmission members 41A and 41C transmit driving forces to the joint 31.

The second transmission member 43 is a rod-shaped member that moves in the same direction as the second intermediate transmission member 25 along the central axis O2 under a driving force from the second intermediate transmission member 25 at the time of the advance of the second intermediate transmission member 25 of the intermediate member 3 coupled in the coupling end surface 4d. In the present embodiment, the second transmission member is substantially bar-shaped as a whole, and has a cross-sectional shape of width W1×thickness H4. However, one lateral surface of the second transmission member 43 is formed with a rack portion 43a having the same shape as the rack portion 41a of the first transmission member 41. Additionally, the thickness H4 is set to be equal to or less than the thickness h2 of the second intermediate transmission member 25.

As a material of the second transmission member 43, the material including proper rigidity in order to transmit a driving force is preferable; for example, metal can be used.

An operating member 44, which regulates the advancing and retracting amounts of the second transmission member 43 and manually operates the position of the second transmission member 43 from the outside, is provided so as to protrude from the lateral surface of the second transmission member 43 on the back surface side of the rack portion 43a.

The second transmission member 43 having such a configuration is housed in the guide groove 4k that slidably holds the second transmission member 43, in a state where the rack portion 43a is directed to the radial inner side.

The guide groove 4k is a groove portion that extends to penetrate in the direction along the central axis O4 inside the second transmission member housing portion 4c, and has a groove bottom surface that slides on the lateral surface of the second transmission member 43 opposite the rack portion 43a, and a groove lateral surface that guides a lateral surface of the second transmission member 43 adjacent to the rack portion 43a.

In the groove bottom surface of the guide groove 4k, a long-hole-shaped stopper groove 4b penetrates along the longitudinal direction of the guide groove. The operating member 44 of the second transmission member 43 is inserted through the inside of the stopper groove 4b.

For this reason, a range where the second transmission member 43 can advance and retract is regulated by the opening amount of the stopper groove 4b in the longitudinal direction.

A protrusion 4n that protrudes toward the second transmission member 43 is provided on a groove lateral surface of the guide groove 4k except for the proximal end side of the guide groove 4k. A range where the protrusion 4n is not provided is a range where the second intermediate transmission member 25 can advance from the coupling end surface 4d.

Meanwhile, the lateral surface of the second transmission member 43 is provided with a step portion 43c that engages the protrusion 4n, and thereby, the lateral surface of the second transmission member 43 opposite the rack portion 43a is able to come into close contact with and slide on the groove bottom surface of the guide groove 4k when the second transmission member 43 advances and retracts.

The guide grooves 4i and 4k may include two separate rectangular guide holes adapted to the outer shapes of the first transmission member 41 and the second transmission member 43, respectively. In the present embodiment, however, the guide grooves are constituted by rectangular cross-sectional grooves that communicate with each other in the radial direction, open to the engaging hole 4e, and are long in the radial direction. That is, the guide groove 4k is formed at the groove bottom portion of the rectangular groove on the radial inner side, and the guide groove 4 i is formed at the opening portion of the groove on the radial outer side.

For this reason, rod-shaped members having a larger cross-sectional area than the first transmission member 41 and the second transmission member 43 can be inserted into the guide grooves 4 i and 4k if the rod-shaped members have a width that is equal to or less than the width W1 of the guide grooves in the circumferential direction.

The pinion 42 is a gear that engages the rack portion 41a of the first transmission member 41 and the rack portion 43a of the second transmission member 43.

A rotating shaft 42a of a pinion 42 is rotatably supported at a substantially constant position from the coupling end surface 4d, in a state where the rotating shaft is biased to the proximal end side of the surgical tool unit 4.

In the present embodiment, as shown in FIG. 13B, a guide hole 4m that extends in the direction along the central axis O4 (not shown in FIG. 13B, and refer to FIG. 13A) is provided in the second transmission member housing portion 4c and the proximal portion 4a that cover the pinion 42 from the side, and the rotating shaft 42a is rotatably supported by a sliding block 42b that is slidably held within the guide hole 4m.

The sliding block 42b is biased toward the proximal end side by the coil spring 18 (surgical-tool-unit-side biasing member) that is arranged on the distal end side (left side shown in FIG. 13B) within the guide hole 4m.

For this reason, since the pinion 42 is biased to the proximal end side even if there is backlash between the rack portions 41a and 43a, the pinion engages the rack portions 41a and 43a without rattling.

Additionally, the coil spring 18 within the guide hole 4m also biases the whole first transmission member 41 and the whole second transmission member 43 to the proximal end side.

In the present embodiment, two sets of reciprocation drive units 40 having such a configuration, as shown in FIG. 11, are provided so as to face each other, in biaxial directions orthogonal to the central axis O4. Additionally, even in any reciprocation drive unit 40, the first intermediate transmission member 26 is arranged on the center side of the coupling end surface 4d compared to the second intermediate transmission member 25. Additionally, when a direction in which the first intermediate transmission member 26 and the second intermediate transmission member 25 are coupled together in the coupling end surface 4d is defined as an arrangement direction of the reciprocation drive unit 40, the respective reciprocation drive units 40 are radially arranged around the central axis O4 of the surgical tool unit 4.

Additionally, as shown in FIG. 14, the coupling protrusion 28 of the surgical tool drive unit 2 is inserted into the engaging hole 3c of the intermediate member 3, the coupling protrusion 27 of the intermediate member 3 is inserted into the engaging hole 4e of the surgical tool unit 4, and the coupling end surfaces 2d and 3B and the coupling end surfaces 3A and 4d are pushed in so as to respectively abut against each other. Accordingly, the respective engaging portions 20 are locked to the locking surfaces 3g and 4g. In this way, in the present embodiment, coupling is completed by the surgical tool drive unit 2, the intermediate member 3, and the surgical tool unit 4 being arranged coaxially with the respective central axes O2, O3, and O4 and being inserted in the directions along the respective central axes.

Accordingly, as shown in FIG. 2, the surgical tool unit 4, the intermediate member 3 and the surgical tool drive unit 2 are coupled together, and thus, the medical manipulator 1 is assembled.

At this time, the surgical tool unit 4, the intermediate member 3, and the surgical tool drive unit 2 are positioned around the central axes O4, O3, and O2 by the coupling protrusions 27 and 28, and the arrangement positions of the reciprocation drive units 40, the guide holes 3d and 3e, and the reciprocation drive units 10 that are radially arranged are aligned with each other.

For this reason, the positions of the groove bottom surfaces of the guide grooves 4k, the guide holes 3d, and the guide grooves 2j on the radial outer side and the positions of the respective groove lateral surfaces in the circumferential direction are aligned with each other. Additionally, the positions of the groove bottom surfaces of the guide grooves 4i, the guide holes 3e, and the guide grooves 2k on the radial inner side are aligned with each other. Additionally, the positions of the respective groove lateral surfaces of the guide grooves 4i, the guide holes 3e, and the guide grooves 2k in the circumferential direction are aligned with each other.

Additionally, the respective reciprocation drive units 10 and 40 face each other via the second intermediate transmission member 25 and the first intermediate transmission member 26 of the intermediate member 3. Additionally, the pinion 42 is biased to the proximal end side by the coil spring 18 that biases the rotating shaft 42a.

For this reason, as shown in FIG. 15, a distal end portion of the first input member 11 and a proximal end portion of the first transmission member 41 abut against a proximal end portion and a distal end portion of the first intermediate transmission member 26, respectively.

Additionally, a distal end portion of the second input member 13 and a proximal end portion of the second transmission member 43 abut against a proximal end portion and a distal end portion of the second intermediate transmission member 25, respectively.

The operation when the medical manipulator 1 configured as described above is used will be described taking a case where the medical manipulator is, for example, attached to one of the above-described slave arms 200a to 200d, the slave arm 200a as an example.

Figure 16A:
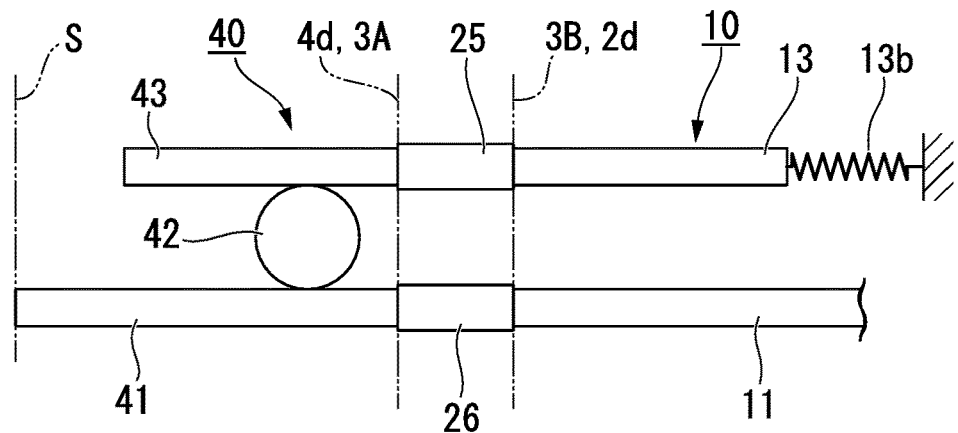
FIG. 16A is a schematic operation explanatory view of the main portions of the medical manipulator of the first embodiment of the present invention.
Figure 16B:
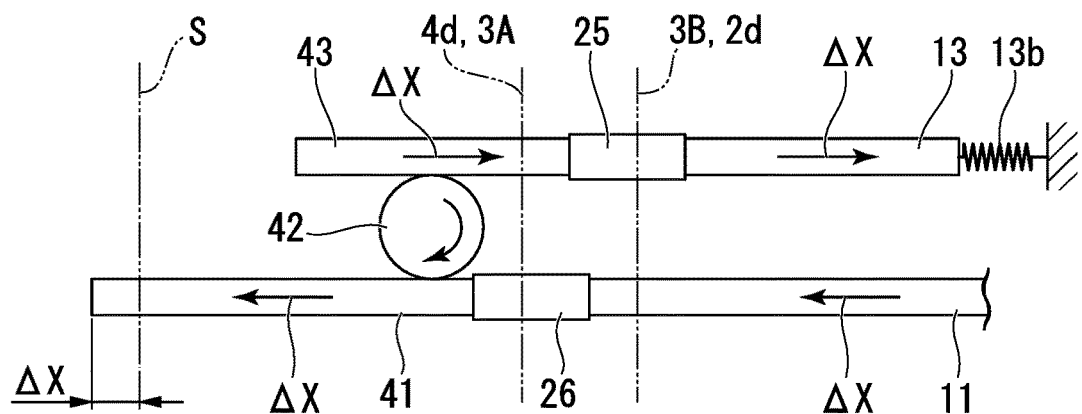
FIG. 16B is a schematic operation explanatory view of the main portions of the medical manipulator of the first embodiment of the present invention.
Figure 16C:
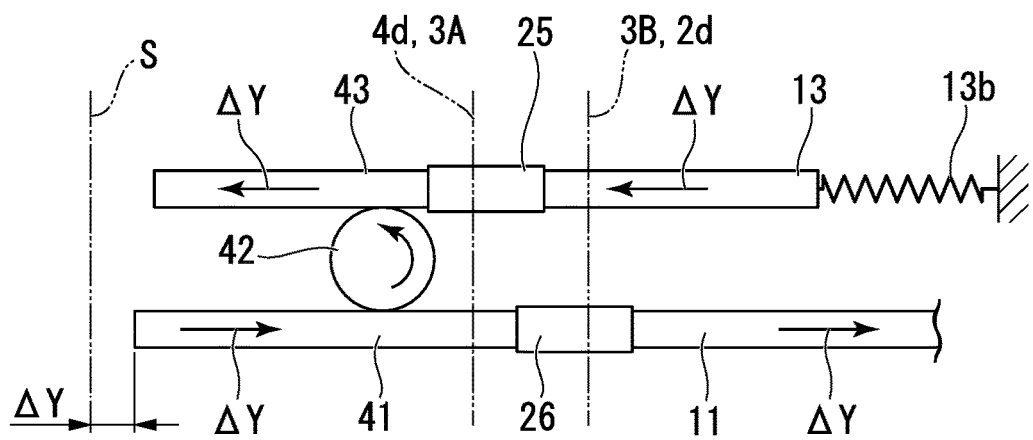
FIG. 16C is a schematic operation explanatory view of the main portions of the medical manipulator of the first embodiment of the present invention.

FIGS. 16A, 16B, and 16C are schematic operation explanatory views of main portions of the medical manipulator of the first embodiment of the present invention.

First, in the above-described medical manipulator system, the operator Op mounts the medical manipulator 1 assembled as described above instead of the surgical tool 240a, the adapter 220a, and the slave arm 200a, and electrically connects the surgical tool drive unit 2 to the slave control circuit 400. Additionally, the surgical tools 240b to 240d that are the other surgical tools are connected to the adapters 220b to 220d if necessary.

If the operator Op performs a predetermined operation on a corresponding master arm, the power unit of a relevant slave arm is driven via the slave control circuit 400a. The power generated in the relevant power unit is converted into a linear motion or a rotary motion via an adapter.

For example, if the operation using the medical manipulator 1 is input, each motor 16 of the surgical tool drive unit 2 is rotated according to an operation amount.

The rotary motion of each motor 16 is converted into a corresponding linear motion by each linear motion converter 15, thereby advancing and retracting the proximal end shaft portion 11b (refer to FIG. 15) of the first input member 11 connected to each linear motion converter 15 in the direction along the central axis O2.

When the motor 16 is stopped, as shown in FIG. 16A, the first input member 11 and the first intermediate transmission member 26 face each other and the second input member 13 and the second intermediate transmission member 25 face each other, in the coupling end surfaces 2d and 3B, and the first intermediate transmission member 26 and the first transmission member 41 face each other and the second intermediate transmission member 25 and the second transmission member 43 face each other, in the coupling end surfaces 3A and 4d.

The distal end portion of the first transmission member 41 coupled to a link of an effector or the like is located at an initial position S.

Additionally, although not particularly shown in the view 16A, the guide grooves 4k, the guide holes 3d, and the guide grooves 2j; and the guide grooves 4i, the guide holes 3e and the guide grooves 2k are all aligned with each other as described above. For this reason, in the coupling end surfaces 2d and 3B, the first input member 11 and the first intermediate transmission member 26, and the second input member 13 and the second intermediate transmission member 25 are able to advance toward and retract from each other in the axial direction. Additionally, in the coupling end surfaces 3A and 4d, the intermediate transmission member 26 and the first transmission member 41, and the second intermediate transmission member 25 and the second transmission member 43 are able to advance toward and retract from each other in the axial direction.

First, as shown in FIG. 16B, when the first input member 11 has advanced to the distal end side by ΔX, the proximal end portion of the first intermediate transmission member 26 receives a driving force by being pressed from the first input member 11, and therefore moves to the distal end side.

Additionally, the proximal end portion of the first transmission member 41 that abuts against the distal end side of the first intermediate transmission member 26 receives a driving force by being pressed from the first intermediate transmission member 26. Since the compression rigidity of the first input member 11, the first intermediate transmission member 26, and the first transmission member 41 is sufficiently large compared to the driving force, even if a compressive stress is generated in the respective members due to the load of the effector, the amount of compressive deformation is negligible compared to the ΔX. For this reason, the distal end of the first transmission member 41 also moves from the initial position S to the distal end side by ΔX.

Accordingly, the driving force is transmitted from the first transmission member 41 to the effector, and the effector is driven.

Meanwhile, when the first input member 11 and the first transmission member 41 move to the distal end side, the pinion 42 engaged with each rack portion 41a is rotated in the clockwise rotation shown in the drawing. As a result, the driving force transmitted to the first input member 11 and the first transmission member 41 is also transmitted to the second input member 13 and the second transmission member 43 via the pinion 42.

Accordingly, the second input member 13 and the second transmission member 43 retract by ΔX to the proximal end side that is a direction opposite to the first input member 11 and the first transmission member 41, and the second intermediate transmission member 25 sandwiched between the second input member 13 and the second transmission member 43 also retracts by ΔX to the proximal end side.

Next, as shown in FIG. 16C, when the first input member 11 has retracted by ΔY from the state of FIG. 16A to the proximal end side, the first input member 11 tends to separate from the proximal end portion of the first intermediate transmission member 26. Therefore, a driving force is not directly transmitted from the first input member 11 to the first intermediate transmission member 26.

However, as the second input member 13 is pressed to the distal end side by the biasing force of the biasing member 13b when the first input member 11 retracts, the second input member 13 presses the second transmission member 43 to the distal end side. Moreover, a driving force is transmitted from the second transmission member 43 via the pinion 42 to the first transmission member 41. That is, a driving force and a displacement are reversed and transmitted from the second transmission member 43 to the first transmission member 41 by the pinion 42, and the first transmission member 41 retracts by ΔY.

Accordingly, the distal end portion of the first transmission member 41 retracts by ΔY from the initial position S, the driving force is transmitted to the effector, and the effector is driven.

Meanwhile, since the distal end portion of the first intermediate transmission member 26 is pressed and retracted by ΔY to the proximal end side by the proximal end portion of the first transmission member 41, the first intermediate transmission member 26 retracts by ΔY and the abutment state between the first intermediate transmission member 26 and the first input member 11 is maintained.

In this way, according to the medical manipulator 1 of the present embodiment, when the first input member 11 is advanced to the distal end side or retracted to the proximal end side, the first transmission member 41 can advance and retract so as to follow the movement of the first input member 11 because the reciprocation drive units 10 and 40 include the action of reversing a driving force and a displacement.

In the medical manipulator 1, the first input member 11 and the second input member 13 are arranged in a pair on the coupling end surface 2d that is an end portion in a direction of attachment and detachment with respect to the surgical tool unit 2, are enabled to advance and retract in mutually opposite directions, and constitute an input member that transmits a driving force in an advance direction when advancing to the surgical tool unit 4 side.

Additionally, the pinion 42 is engaged with the first transmission member 41 and the second transmission member 43. Additionally, the pinion 42 constitutes a surgical-tool-unit-side reversal interlinking member that reverses a moving direction of the first transmission member or the second transmission member and transmits the displacement of one of the first transmission member 41 and the second transmission member 43 to the other of the first transmission member 41 and the second transmission member 43 in a reversed moving direction.

In this way, since the surgical-tool-unit-side reversal interlinking member is included, the first transmission member 41 and second transmission member 43 can be advanced and retracted via the biasing member 13b, the first input member 11, and the second input member 13 by the motor 16 that is one drive source.

Next, the attachment and detachment operation of the medical manipulator 1 will be described.

In the medical manipulator 1, the coupling protrusion 28, the engaging hole 3c, the coupling protrusion 27, and the engaging hole 4e extend parallel to the central axes O2, O3, and O4, of the corresponding surgical tool drive unit 2, intermediate member 3, and surgical tool unit 4, respectively, and the directions along each of the central axes O2, O3, and O4 are attachment and detachment directions.

Additionally, the first input member 11, the first intermediate transmission member 26, and the first transmission member 41, and the second input member 13, the second intermediate transmission member 25, and the second transmission member 43 are also arranged parallel to the corresponding central axes O2, O3, and O4, respectively.

For this reason, as described above, coupling is performed by the surgical tool drive unit 2, the intermediate member 3, and the surgical tool unit 4 being arranged coaxially with the respective central axes O2, O3, and O4 and being inserted in the directions along the respective central axes.

In that case, in the above description, as shown in FIG. 15, a case where coupling is performed in a state where the end portions of the first input member 11 and the second input member 13 are aligned with the coupling end surface 2d, the end portions of the first intermediate transmission member 26 and the second intermediate transmission member 25 are aligned with the coupling end surfaces 3A and 3B, respectively, and the end portions of the first transmission member 41 and 43 are aligned with the coupling end surface 4d has been described. However, the end portions of the input members, the intermediate transmission members, and the transmission members can be easily coupled together even in a state where these members have advanced and retracted with respect to the respective coupling end surfaces.

In order to remove the surgical tool unit 4 from the intermediate member 3, the pair of release buttons 21 protruding to the sides of the surgical tool unit 4 are pushed in to the inner side, respectively. Accordingly, the end portions of the respective shaft portions 21b press the engaging arm portions 20A and 20B toward the central axis O4, and release the locking between the engaging claw portions 20b and the locking surfaces 4g. Accordingly, it is possible to separate the surgical tool unit 4 and the intermediate member 3 from each other in the directions along the central axes O4 and O3.

In that case, the first transmission member 41 and the first intermediate transmission member 26 only abut against each other in the direction along the central axis O4, and the second transmission member 43 and the second intermediate transmission member 25 only abut against each other in the direction along the central axis O3. For this reason, the first transmission member 41 and the first intermediate transmission member 26 can be easily separated from each other and the second transmission member 43 and the second intermediate transmission member 25 can also be easily separated from each other, even in a state where these members have advanced and retracted with respect to the coupling end surfaces 4d and 3A.

For this reason, the surgical tool unit 4 can be removed from the intermediate member 3 simply by the operation of pushing in the release buttons 21 and separating the surgical tool drive unit 2 and the intermediate member 3 from each other in the axial direction.

In addition, in this removal operation, the intermediate member 3 may be in the state of being mounted on the surgical tool drive unit 2, or may be in a state of being removed from the surgical tool drive unit 2 in advance.

Similarly, in order to remove the intermediate member 3 from the surgical tool drive unit 2, the pair of release buttons 21 protruding to the sides of the intermediate member 3 are pushed in to the inner side, respectively. Accordingly, the end portions of the respective shaft portions 21 press the engaging arm portions 20A and 20B toward the central axis O3, and release the locking between the engaging claw portions 20b and the locking surfaces 3g. Accordingly, it is possible to separate the intermediate member 3 and the surgical tool drive unit 2 from each other in the directions along the central axes O3 and O2.

In that case, since the first intermediate transmission member 26 and the first input member 11, and the second intermediate transmission member 25 and the second input member 13 only abut against each other in the directions along the central axes O3 and O2, respectively, these members can be easily separated from each other even in a state where the members have advanced and retracted with respect to the coupling end surfaces 3B and 2d.

For this reason, the intermediate member 3 can be removed from the surgical tool drive unit 2 simply by the operation of pushing in the release buttons 21 and separating the intermediate member 3 and the surgical tool drive unit 2 from each other in the axial direction.

In this removal operation, the intermediate member 3 may be in the state of being mounted on the surgical tool unit 4, or may be in the state of being removed from the surgical tool unit 4 in advance.

When the surgical tool unit 4 is removed from the surgical tool drive unit 2, a driving force is no longer transmitted to the first transmission member 41. In the present embodiment, however, since the operating member 44 is provided at the second transmission member 43, a driving force can be transmitted to the first transmission member 41 by manually adjusting the position of the operating member 44.

For this reason, for example, when the surgical tool unit 4 is removed and kept, it is easy to change the opening/closing state of the forceps portion 30 or to change bending of the joint 31 even after the removal. Additionally, it is easy to adjust the advance and retract positions of the first transmission member 41 and the second transmission member 43 and store the members so as to align with the coupling end surface 4d.

Thus, since the advance and the retract directions of the input members, the intermediate transmission members, and the transmission members are parallel to the attachment and detachment directions in the medical manipulator 1, coupling can be performed simply by pushing the members along the axial direction at the time of coupling. In the case of the removal, the members may be simply separated from each other along the axial direction after the operation of pushing in the release buttons 21 is performed. For this reason, since operations, such as a rotational operation, do not occur for, for example, insertion or coupling, attachment and detachment can be easily and rapidly performed.

According to the medical manipulator 1 of the present embodiment, a driving force is transmitted by arranging the input members that transmit the driving force from the surgical tool drive unit to the surgical tool unit so as to face the input members and the first and second transmission members at the end portions in the attachment and detachment directions. Accordingly, attachment and detachment can be performed by movement only in the attachment and detachment directions, and the attachment and detachment of the surgical tool unit with respect to the surgical tool drive unit can be easily and rapidly performed.

Second Embodiment

Figure 17:
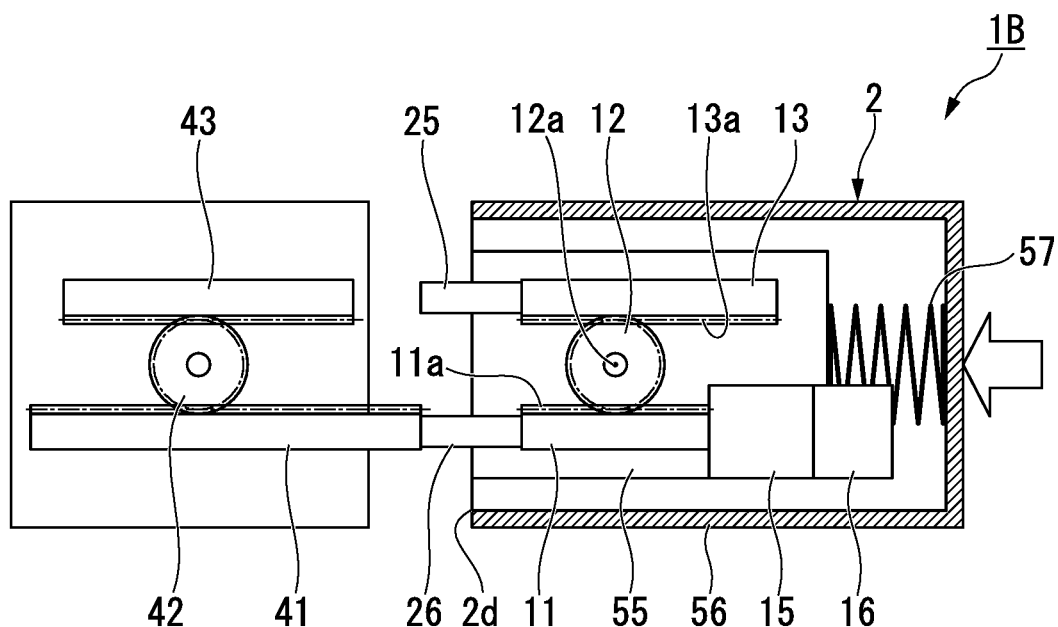
FIG. 17 is a schematic view of a medical manipulator of a second embodiment of the present invention.
Figure 18:
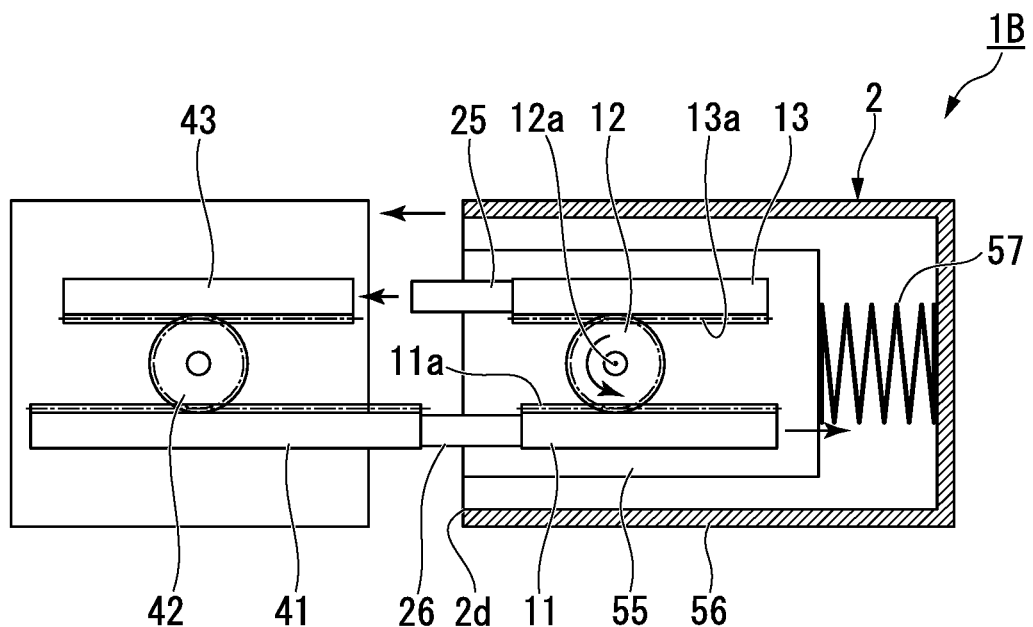
FIG. 18 is a view showing the action of the medical manipulator of the second embodiment of the present invention.
Figure 19:
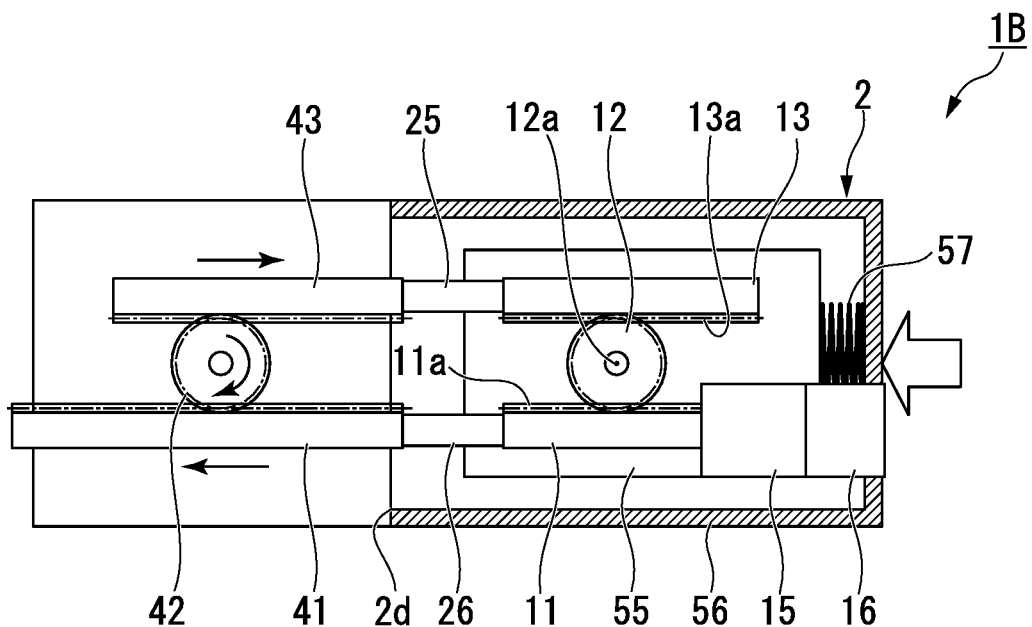
FIG. 19 is a schematic view showing another configuration example of the embodiment.

Next, a second embodiment will be described. FIG. 17 is a schematic view showing main portions of a medical manipulator of the present embodiment. FIG. 18 is a view showing the action of the medical manipulator of the present embodiment.

A medical manipulator 1B of the present embodiment, as main portions are schematically shown in FIG. 17, includes a base 55 to which the first input member 11 and the second input member 13 are coupled so as to be capable of advancing and retracting, a housing 56 that holds the base 55 therein, and biasing member 57 (second biasing member) that is coupled to the base 55 and the housing 56 so as to bias the base 55 to the distal end side with respect to the housing 56.

Additionally, the linear motion converter 15 and first input member 11 can be attached and detached in an arbitrary positional relationship.

Moreover, the present embodiment includes a rack 11a that is formed at the first input member 11, a rack 13a that is formed at the second input member 13, and a pinion 12 that engages the rack 11a of the first input member 11 and the rack 13a of the second input member 13 and couple the first input member 11 and the second input member 13 together.

That is, in the present embodiment, the rack and pinion mechanism operates so that the advance and the retract directions of the first input member 11 and the second input member 13 are reversed to each other.

The pinion 12 is a gear that engages the rack 11a of the first input member 11 and the rack 13a of the second input member 13. The pinion 12 is engaged with the first input member 11 and the second input member 13, and constitutes a drive-unit-side reversal interlinking member that reverses a moving direction of the first transmission member or the second transmission member and transmits the displacement of the first input member 11 to the second input member 13.

Since the drive-unit-side reversal interlinking member is included in this way, the first input member 11 and the second input member 13 can be advanced and retracted via the linear motion converter 15 by the motor 16 that is one drive source.

A rotating shaft 12a of the pinion 12 is rotatably supported at a substantially constant position from the coupling end surface 2d, in a state where the rotating shaft is biased at the distal end side of the surgical tool drive unit 2.

In the present embodiment, the first input member 11 and the second input member 13 are pressed against the first transmission member 41 and second transmission member 43 when the surgical tool unit 4 is attached to the surgical tool drive unit 2. Here, when gaps are produced between a distal end of the first input member 11 and a proximal end of the first transmission member 41 and between a distal end of the second input member 13 and a proximal end of the second transmission member 43, these gaps are eliminated as the biasing member 57 contracts. As a result, the distal end of the first input member 11 and the proximal end of the first transmission member 41 come into close contact with each other, and the distal end of the second input member 13 and the proximal end of the second transmission member 43 come into close contact with each other.

Since the distal end of the first input member 11 and the proximal end of the first transmission member 41 come into close contact with each other and the distal end of the second input member 13 and the proximal end of the second transmission member 43 come into close contact with each other, the effector can be operated similar to the above-described first embodiment even in the present embodiment.

In the present embodiment, since the linear motion converter 15 and the first input member 11 are fixed in a constant positional relationship, the above-described gaps are eliminated as the relative positional relationship between the first transmission member 41 and the second transmission member 43 varies in addition to the action of the biasing member 57.

Third Embodiment

Figure 20:
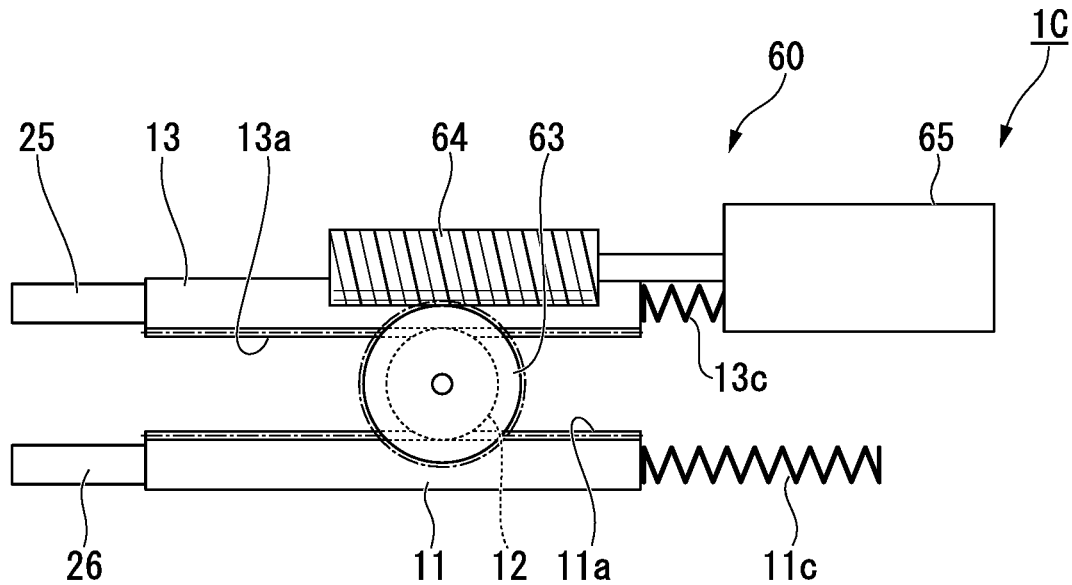
FIG. 20 is a schematic plan view showing a medical manipulator of a third embodiment of the present invention.
Figure 21:
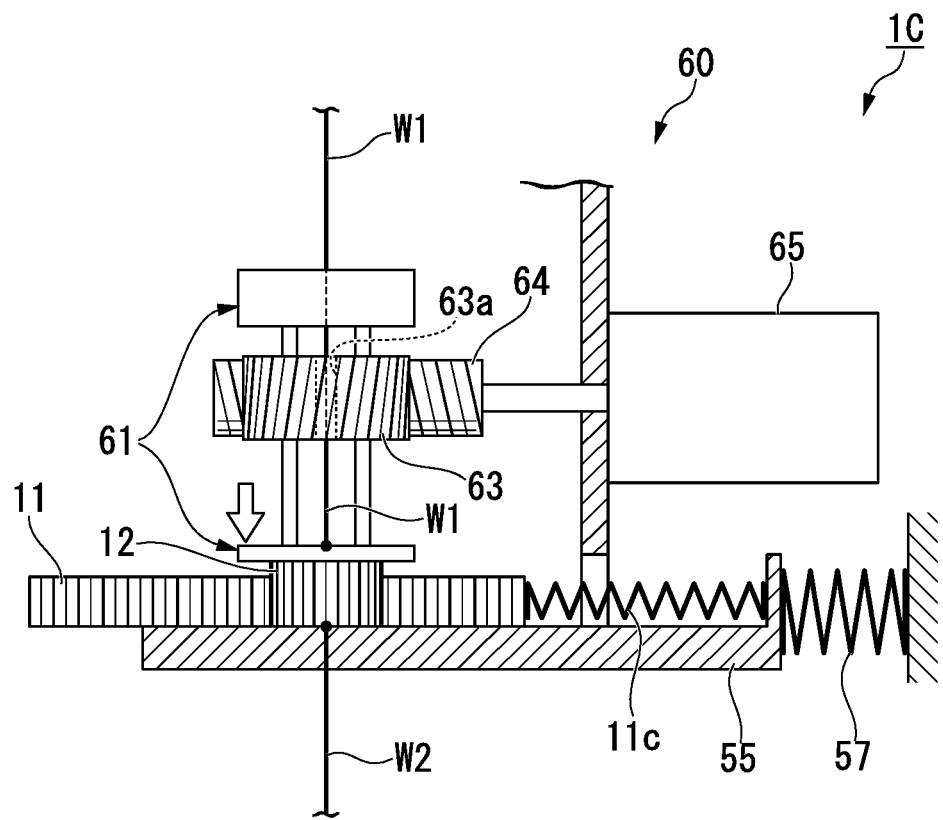
FIG. 21 is a schematic side view showing the medical manipulator.
Figure 22:
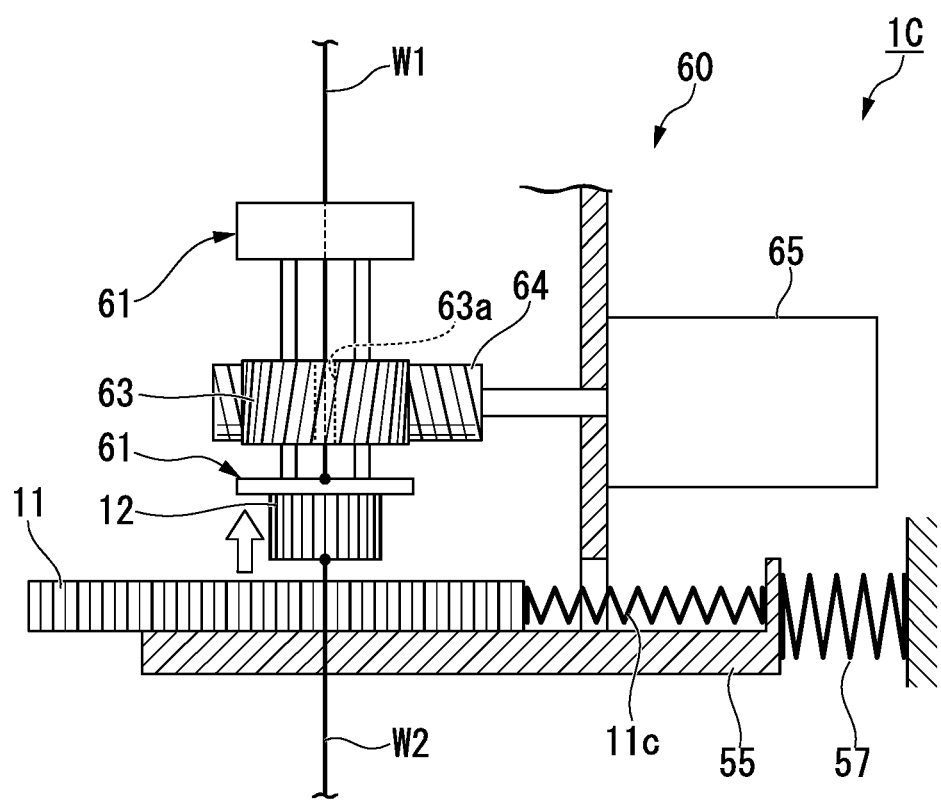
FIG. 22 is a view showing the action of the medical manipulator.
Figure 23:
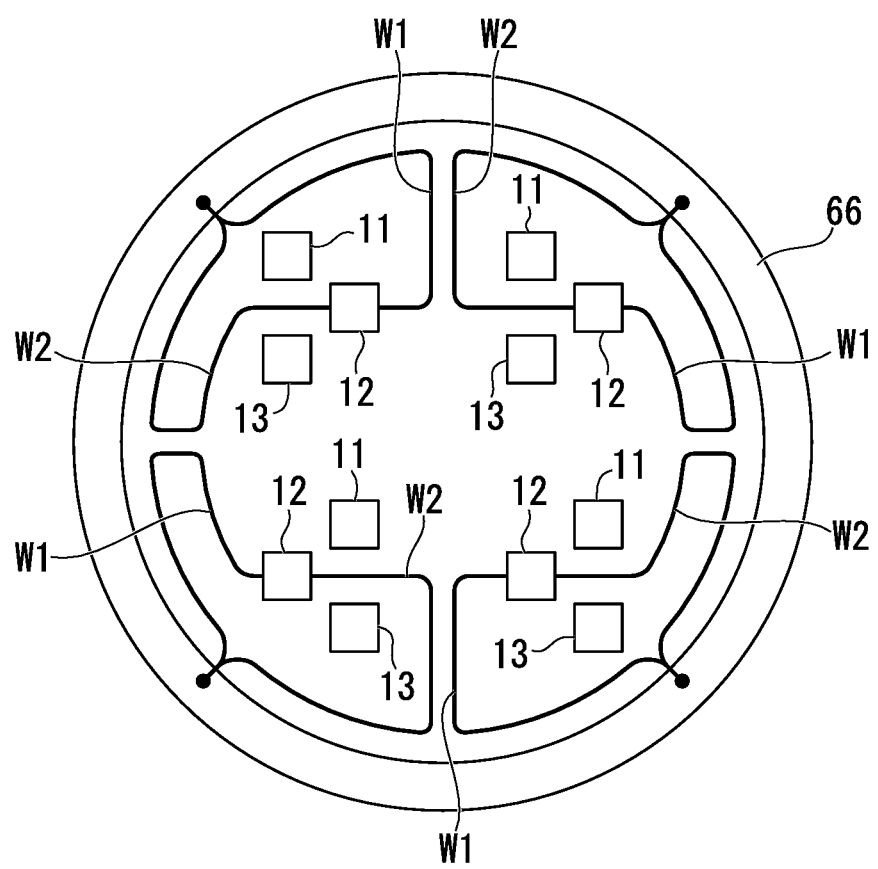
FIG. 23 is a schematic view showing the configuration of wires and a slider for being caused to be simultaneously engaged with or disengaged from a plurality of pinions in the medical manipulator.

Next, a medical manipulator of a third embodiment of the present invention will be described. FIG. 20 is a schematic plan view showing the medical manipulator of the present embodiment. FIG. 21 is a schematic side view showing the medical manipulator of the present embodiment. FIG. 22 is a view for describing the action of the medical manipulator of the present embodiment. FIG. 23 is a schematic view showing the configuration of wires and a slider for simultaneously moving a plurality of pinions.

A medical manipulator 1C shown in FIG. 20 has a configuration in which the surgical tool unit 4 and the surgical tool drive unit 2 are coupled together, similar to the configuration described in the second embodiment.

Additionally, as shown in FIGS. 20 and 21, the medical manipulator 1C of the present embodiment does not have the biasing member 13b, the linear motion converter 15 (drive source), or the motor 16 (drive source). Moreover, the medical manipulator 1C of the present embodiment includes the pinion 12 that engages the rack 11a of the first input member 11 and the rack 13a of the second input member 13 and couples the first input member 11 and the second input member 13 together, and an actuator 60 with an engaging and disengaging mechanism that changes the engagement states between the racks 11*a* and 13*a* and the pinion 12 and rotationally operates the pinion 12. In addition, in the present embodiment, the first input member 11, the second input member 13, and the actuator 60 with an engaging and disengaging mechanism are provided on a base 55, and the base 55 is biased to the distal end side by biasing member 57.

Additionally, in the present embodiment, the first input member 11 is provided with biasing member 11*c* (first drive-unit-side biasing member) that biases the first input member 11 toward the distal end side. Moreover, in the present embodiment, the second input member 13 is provided with biasing member 13*c* (second drive-unit-side biasing member) that biases the second input member 13 toward the distal end side.

The biasing member 11*c* and 13*c* have weak biasing forces that are less than biasing forces that move the first transmission member 41 and the second transmission member 43.

When the surgical tool unit 4 is attached to the surgical tool drive unit 2, the first input member 11 and the second input member 13 are pressed against the first transmission member 41 and second transmission member 43 by the biasing forces of the biasing member 11*c* and 13*c* before the pinion 12 engages the racks 11*a* and 13*a*.

Although an example including the biasing member 11*c* and 13*c* has been described in the present embodiment, the biasing member 11*c* and 13*c* do not have to be provided. The attachment in this case is performed by directing the surgical tool drive unit 2 and the surgical tool unit 4 downward and pressing the first input member 11 and the second input member 13 against the first transmission member 41 and the second transmission member 43 due to gravity, before the pinion 12 engages the racks 11*a* and 13*a*.

The actuator 60 with an engaging and disengaging mechanism has a guide 61 that supports the pinion 12 so as to be capable of advancing and retracting the pinion in the direction of a rotation center of the pinion 12, a worm wheel 63 for rotating the pinion 12 together with the guide 61, a worm gear 64 that engages the worm wheel 63, and a motor 65 that rotationally operates the worm gear 64.

The guide 61 is configured so as to be capable of performing switching between a state where the pinion 12 has engaged the racks 11*a* and 13*a* and a state where the pinion 12 has disengaged from both of the racks 11*a* and 13*a*, for example, by advancing and retracting the pinion 12 in the direction of the rotation center by a manual operation. In the present embodiment, the guide 61 is provided with a wire w1 for moving the pinion 12 in the direction of the rotating shaft of the pinion. Additionally, the pinion 12 is provided with a wire w2 for moving the pinion 12 in the direction of the rotating shaft of the pinion.

The wire w1 provided at the guide 61 is pulled out from a side where the pinion 12 is disposed to an opposite side thereof through a through hole 63*a* formed in the worm wheel 63.

By pulling the wire w1 and the wire w2, respectively, the pinion 12 advances and retracts in the direction of the rotating shaft of the pinion.

Additionally, as shown in FIG. 23, a slider 66 that collectively pulls the wires w1 and w2 that guide the respective pinions, respectively, may be provided, for example, for the purpose of simultaneously advancing and retracting a plurality of the pinions 12.

In the present embodiment, in a state where the pinion 12 has engaged the racks 11*a* and 13*a*, an effector 30 operates as described in the above-described first embodiment as the motor 65 rotationally operates. Additionally, in a state where the pinion 12 has disengaged from both of the racks 11*a* and 13*a*, a driving force is not transmitted to the effector 30 even if the motor 65 rotationally operates.

Additionally, as shown in FIGS. 20 and 22, the first input member 11 and the second input member 13 are able to advance and retract in a state where the pinion 12 has disengaged from both of the racks 11*a* and 13*a* and in a state where the surgical tool unit 4 is removed from the surgical tool drive unit 2.

The action of the medical manipulator 1C of the present embodiment will be described.

When the effector 30 is used in the medical manipulator 1C of the present embodiment, the distal end portion of the first input member 11 and the proximal end portion of the first transmission member 41 directly face each other and abut against each other, and the distal end portion of the second input member 13 and the proximal end portion of the second transmission member 43 directly face each other and abut against each other (for example, refer to FIG. 16). Moreover, as shown in FIGS. 20 to 22, since the pinion 12 is engaged with the racks 11*a* and 13*a* by the actuator 60 with an engaging and disengaging mechanism, the first input member 11 and the second input member 13 can be operated to advance and retract by rotating the pinion 12.

When the surgical tool unit 4 is attached to the surgical tool drive unit 2, first, the pinion 12 is brought into a state where the pinion has disengaged from the racks 11*a* and 13*a*, and subsequently, the first input member 11 and the first transmission member 41 are coupled together and the second input member 13 and the second transmission member 43 are coupled together, similar to the above-described second embodiment. At this time, the first transmission member 41 and the second transmission member 43 do not move, and the first input member 11 and the second input member 13 move according to the positions of the first transmission member 41 and the second transmission member 43. For this reason, an unnecessary driving force is not applied to the effector 30.

Thereafter, by engaging the pinion 12 with the racks 11*a* and 13*a*, the first input member 11 and the second input member 13 are regulated in operating directions thereof so as to operate to advance and retract in mutually opposite directions, and are operated by the driving force of the motor 65.

The positional relationship between the first transmission member 41 and the second transmission member 43 is determined according to the state of the effector 30 provided at the surgical tool unit 4. Here, for example, in the case of the flexible surgical tool 240*d*, the flexible wires are used, and a treatment is performed within a curved space, such as the alimentary canal. Thus, the state of the effector 30 is influenced by the bent state of the flexible wires connected to the effector 30 in addition to the state of the effector 30 itself. For example, if the flexible wires in the flexible surgical tool 240*d* are pulled, the whole surgical tool 240*d* may be deformed by the flexible wires.

In the present embodiment, when the surgical tool unit 4 is attached to the surgical tool drive unit 2, the surgical tool unit 4 is mounted on the surgical tool drive unit 2 in a state where neither of the first transmission member 41 and the second transmission member 43 operates. As a result, the effector 30 and the whole surgical tool 240*d* including the effector 30 can be prevented from operating uselessly when the surgical tool unit 4 is attached to the surgical tool drive unit 2.

Moreover, the biasing member 57 absorbs deviation of the meshing when the pinion 12 engages the racks 11a and 13a. For this reason, the gap between the first input member 11 and the first transmission member 41 and the gap between the second input member 13 and the second transmission member 43 can be eliminated to prevent backlash from occurring.

Modified Example

Figure 24:
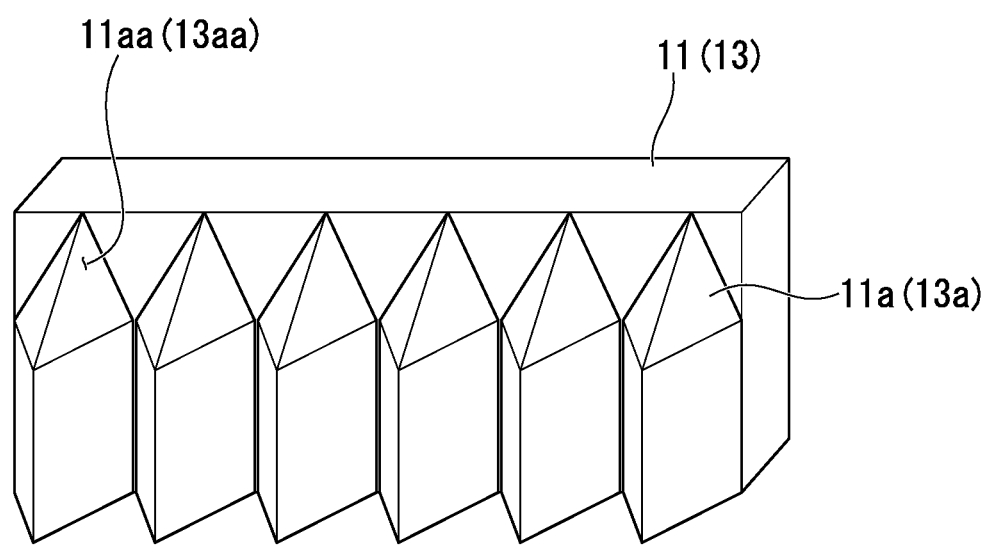
FIG. 24 is a perspective view showing the configuration of a modified example of the embodiment.

Next, a modified example of the above-described embodiment will be described. FIG. 24 is a perspective view showing the configuration of the present modified example.

The present modified example has a feature in the shape of teeth in the racks 11a and 13a.

As shown in FIG. 24, the ends of the racks 11a and 13a on an inlet side when the pinion 12 is inserted have tapered guide portions 11aa and 13aa. The guide portions 11aa and 13aa formed on the racks 11a and 13a can guide the teeth formed on the pinion 12 between the respective teeth of the racks 11a and 13a.

In addition, even in the pinion 12, tapered guide portions may be formed similar to the tapers formed at the racks 11a and 13a.

Fourth Embodiment

Figure 25:
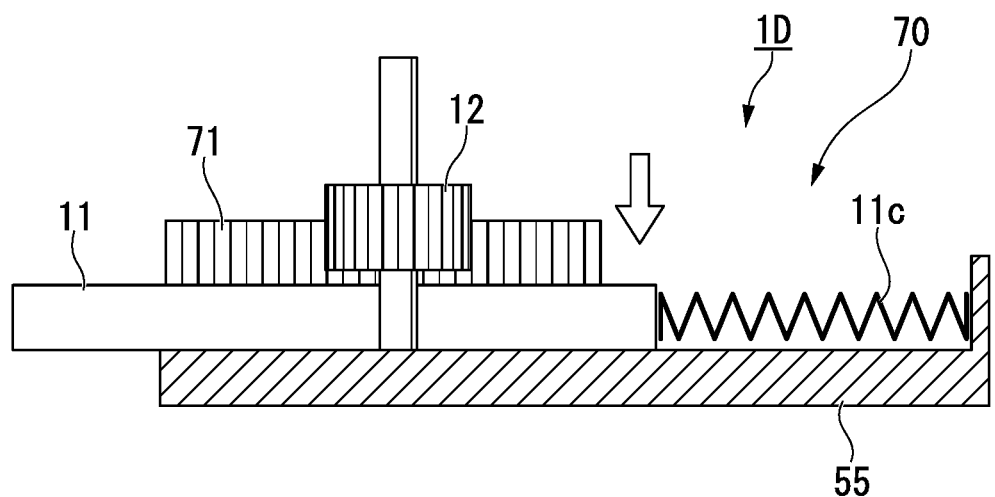
FIG. 25 is a schematic side view showing the configuration of a portion of a medical manipulator of a fourth embodiment of the present invention.
Figure 26:
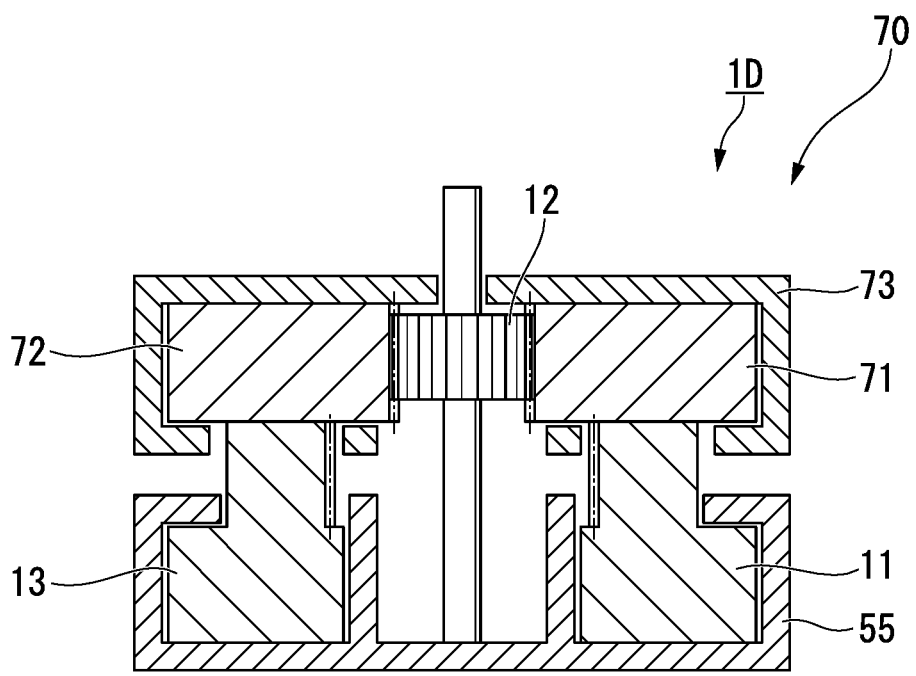
FIG. 26 is a schematic front view showing the configuration of the portion of the medical manipulator of the embodiment.

Next, a fourth embodiment of the present invention will be described. FIG. 25 is a schematic side view showing the configuration of a portion of a medical manipulator of the present embodiment. FIG. 26 is a schematic front view showing the configuration of a portion of the medical manipulator of the present embodiment.

Figure 27:
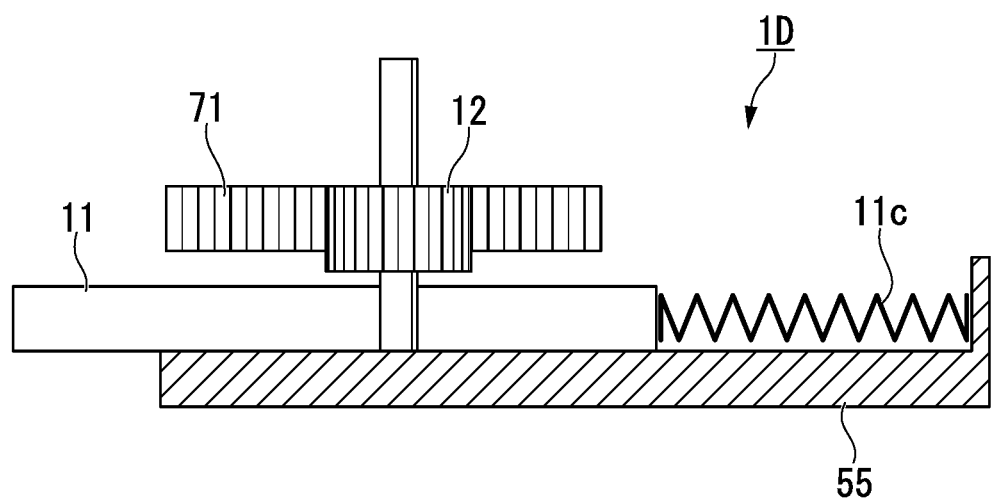
FIG. 27 is a view showing the action of the medical manipulator of the present embodiment.
Figure 28:
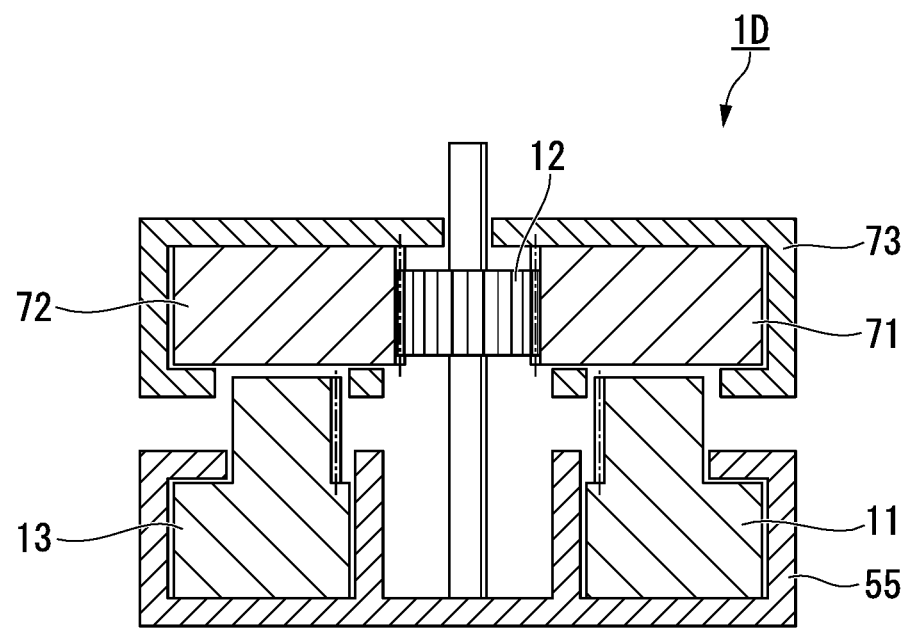
FIG. 28 is a view showing the action of the medical manipulator of the present embodiment.

FIGS. 27 and 28 are views for describing the action of the medical manipulator of the present embodiment.

As shown in FIGS. 25 and 26, a medical manipulator 1D of the present embodiment is different in that an actuator 70 with an engaging and disengaging mechanism having a different configuration is included instead of the actuator 60 with an engaging and disengaging mechanism.

The actuator 70 with an engaging and disengaging mechanism has a first rack 71 capable of advancing and retracting in the same directions as the first input member 11 described in the first embodiment, a second rack 72 capable of advancing and retracting in the same directions as the second input member 13 described in the first embodiment, and a rack holder 73 that holds the first rack 71 and the second rack 72 so as to be capable of advancing and retracting and is coupled to the rotating shaft of the pinion 12.

The rack 71 has a frictional surface that frictionally engages the first input member 11. The rack 72 has a frictional surface that frictionally engages the second input member 13. The pinion 12 couples the rack 71 and the rack 72 together so that the rack 71 and the rack 72 advance and retract in mutually opposite directions.

The rack holder 73 operates to advance and retract the rack 71 and the rack 72 in the direction of the rotating shaft of the pinion 12, thereby switching a state where the rack 71 and the rack 72 have contacted the first input member 11 and the second input member 13 and a state where the rack 71 and the rack 72 have separated from the first input member 11 and the second input member 13.

In addition, even in the present embodiment, the pinion 12 is configured so as rotate as a driving force is transmitted by a motor or the like.

There is a difference in that the pinion 12 is engaged with and disengaged from the racks 11a and 13a in the present embodiment, whereas the rack 71 and the rack 72 is engaged with and disengaged from the first input member 11 and the second input member 13 by friction in the third embodiment.

Even in such a configuration, the same effects as in the above-described third embodiments are exhibited.

Additionally, in the present embodiment, a distance that the rack holder 73 is moved in order to separate the rack 71 and the rack 72 from the first input member 11 and the second input member 13 is reduced.

Fifth Embodiment

Figure 29:
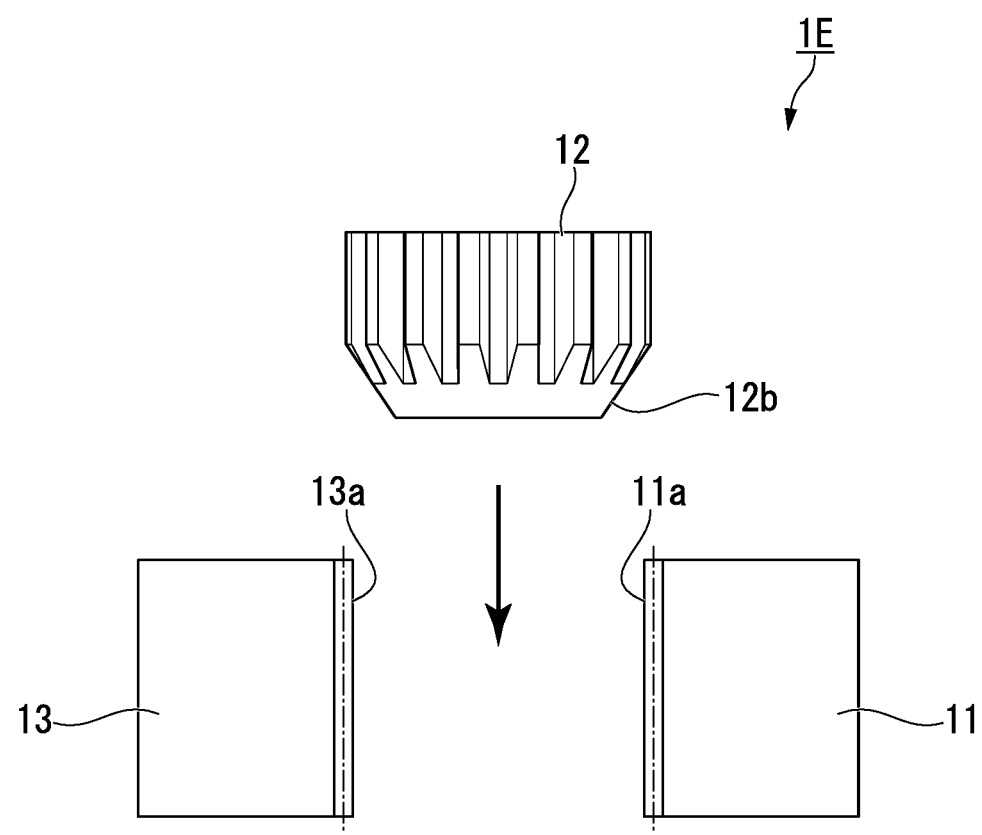
FIG. 29 is a schematic front view showing the configuration of a portion of a medical manipulator of a fifth embodiment of the present invention.

Next, a fifth embodiment of the present invention will be described. FIG. 29 is a schematic front view showing the configuration of a portion of the medical manipulator of the present embodiment.

A medical manipulator 1E of the present embodiment is different from the medical manipulator 1B described in the second embodiment in terms of the shape of the pinion 12.

That is, as shown in FIG. 29, in the medical manipulator 1E of the present embodiment, a tapered inclined surface 12b where the external diameter of the pinion 12 changes gradually is provided at the portion of the pinion 12 that is inserted between the racks 11a and 13a.

The pinion 12 having the inclined surface 12b is configured so that the pinion 12 has a smaller diameter than a gap between the rack 11a and the rack 13a and thereby, the pinion 12 is smoothly inserted between the rack 11a and the rack 13a.

The racks 11a and 13a may be partially inclined so that the size of the gap between the racks 11a and 13a becomes larger than the external diameter of the pinion 12.

Instead of a configuration in which the first input member 11 and the second input member 13 are coupled together by the rack and pinion mechanism, the first input member 11 and the second input member 13 may be coupled together using a roller that frictionally engages the first input member 11 and the second input member 13. For example, a truncated cone-shaped roller that is rotationally driven by a motor or the like, and frictional surfaces formed at the first input member 11 and the second input member 13 so as to contact an outer peripheral surface of this roller may be provided.

While preferred embodiments of the present invention have been described and illustrated above, it should be understood that these are exemplary of the present invention and are not to be considered as limiting. Additions, omissions, substitutions, and other modifications can be made without departing from the concept of the present invention.

The invention claimed is:

1. A medical manipulator comprising:
a surgical tool provided with an effector that operates an operation target; and
a surgical tool drive unit detachably provided with respect to the surgical tool for supplying a driving force for driving the effector,
wherein the surgical tool drive unit includes:
a first input rod and a second input rod, the first and second input rods being arranged in a pair at a first end portion in an attachment and detachment direction with respect to the surgical tool, the first and second input rods being capable of advancing and retracting parallel to each other, and transmit the driving force in an advance direction when the first and second input rods are advanced to the surgical tool side, the first input rod being formed separately from the second input rod; and an actuator that causes at least one of the first and second input rods to advance and retract, and wherein the surgical tool includes:

a first transmission rod that faces the first input rod, the first transmission rod being configured to at least indirectly abut a distal end of the first input rod at a first end portion in the attachment and detachment direction with respect to the surgical tool drive unit, moves in a same direction as an advance direction of the first input rod under the driving force from the first input rod, and is connected to the effector at a second end portion;

a second transmission rod formed separately from the first transmission rod, the second transmission rod facing that faces the second input rod, the second transmission rod being configured to at least indirectly abut a distal end of the second input member at the first end portion in the attachment and detachment direction with respect to the surgical tool drive unit, and moves in a same direction as an advance direction of the second input rod under the driving force from the second input rod; and a surgical-tool-side reversal interlinking member engaged with both the first transmission rod and with the second transmission rod, the surgical-tool-side reversal interlinking member being configured to reverse a moving direction of the first transmission rod or the second transmission rod and transmits a displacement of one of the first transmission rod and the second transmission rod to the other of the first transmission rod and the second transmission rod;

wherein the surgical tool drive unit has a drive-unit-side biasing member that biases the second input rod toward the first end portion in the attachment and detachment direction with respect to the surgical tool.

2. The medical manipulator according to claim 1, wherein the actuator is a motor.

3. The medical manipulator according to claim 1, wherein the surgical-tool-side reversal interlinking member is a rotatable pinion disposed between the first and second transmission rods so as to reverse the moving direction of the first transmission rod or the second transmission rod and transmits the displacement of one of the first transmission rod and the second transmission rod to the other of the first transmission rod and the second transmission rod.

4. The medical manipulator according to claim 1, wherein the rotatable pinion is a pinion gear and at least a portion of the first transmission rod and the second transmission rod engaging with the pinion gear is a gear rack.

5. A medical manipulator comprising:

a surgical tool unit provided with an effector that operates an operation target; and a surgical tool drive unit detachably provided with respect to the surgical tool unit for supplying a driving force for driving the effector, wherein the surgical tool drive unit includes:

a first input rod and a second input rod, the first input rod and the second input rod being arranged in a pair at a first end portion in an attachment and detachment direction with respect to the surgical tool unit, the first and second input rods being capable of advancing and retracting parallel to each other, and transmit the driving force in an advance direction when the first and second input rods are advanced to the surgical tool unit side, the first input rod being formed separately from the second input rod; and a drive source that causes at least one of the first and second input rods to advance and retract, wherein the surgical tool unit includes:

a first transmission rod that faces the first input rod, the first transmission rod being configured to at least indirectly abut a distal end of the first input rod at a first end portion in the attachment and detachment direction with respect to the surgical tool drive unit, moves in a same direction as an advance direction of the first input rod under the driving force from the first input rod, and is connected to the effector at a second end portion;

a second transmission rod formed separately from the first transmission rod, the second transmission rod facing that faces the second input rod, the second transmission rod being configured to at least indirectly abut against a distal end of the second input rod at the first end portion in the attachment and detachment direction with respect to the surgical tool drive unit, and moves in a same direction as an advance direction of the second input rod under the driving force from the second input rod; and a surgical-tool-unit-side reversal interlinking member engaged with both the first transmission rod and with the second transmission rod, the surgical-tool-unit-side reversal interlinking member being configured to reverse a moving direction of the first transmission rod or the second transmission rod and transmits a displacement of one of the first transmission rod and the second transmission rod to the other of the first transmission rod and the second transmission rod, and wherein the surgical tool drive unit has a drive-unit-side biasing member that biases the second input rod toward the first end portion in the attachment and detachment direction with respect to the surgical tool unit.

6. The medical manipulator according to claim 1, further comprising an engaging portion configured to detachably couple the surgical tool and the surgical tool drive unit.

7. The medical manipulator according to claim 6, wherein the engaging portion comprises a release button configured to release the coupling between the surgical tool and the surgical tool drive unit by operating the release button.

8. The medical manipulator according to claim 5, further comprising an engaging portion configured to detachably couple the surgical tool and the surgical tool drive unit.

9. The medical manipulator according to claim 8, wherein the engaging portion comprises a release button configured to release the coupling between the surgical tool and the surgical tool drive unit by operating the release button.

10. A medical manipulator comprising:

a surgical tool provided with an effector that operates an operation target; and a surgical tool drive unit detachably provided with respect to the surgical tool for supplying a driving force for driving the effector, wherein the surgical tool drive unit includes:

a first input rod and a second input rod, the first and second input rods being arranged in a pair at a first end portion in an attachment and detachment direction with respect to the surgical tool, the first input rod and the second input rod being capable of advancing and retracting parallel to each other only where the driving force is transmitted to the first input rod in an advance direction to the surgical tool side, the first input rod being formed separately from the second input rod; and an actuator that causes the first input rod to advance and retract, and wherein the surgical tool includes:

a first transmission rod that faces the first input rod, the first transmission rod being configured to at least indirectly abut a distal end of the first input rod at a first end portion in the attachment and detachment direction with respect to the surgical tool drive unit, moves in a same direction as an advance direction of the first input rod under the driving force from the first input rod, and is connected to the effector at a second end portion, the first transmission rod not being connected to the first input rod other than the abutment;

a second transmission rod formed separately from the first transmission rod, the second transmission rod facing the second input rod, the second transmission rod being configured to at least indirectly abut a distal end of the second input member at the first end portion in the attachment and detachment direction with respect to the surgical tool drive unit, and moves in a same direction as an advance direction of the second input rod, the second transmission rod not being connected to the second input rod other than the abutment; and a surgical-tool-side reversal interlinking member engaged with both the first transmission rod and with the second transmission rod, the surgical-tool-side reversal interlinking member being configured to reverse a moving direction of the first transmission rod or the second transmission rod and transmits a displacement of one of the first transmission rod and the second transmission rod to the other of the first transmission rod and the second transmission rod;

wherein the surgical tool drive unit has a drive-unit-side biasing member, the drive-unit-side biasing member being configured to bias the second input rod to at least indirectly abut and move the second transmission rod.

\* \* \* \* \*